(12) United States Patent
Pinal et al.

(10) Patent No.: US 11,173,046 B2
(45) Date of Patent: *Nov. 16, 2021

(54) SURGICAL INSERTION INSTRUMENTS

(71) Applicant: Howmedica Osteonics Corp., Mahwah, NJ (US)

(72) Inventors: Frank Pinal, Jersey City, NJ (US); Bryan D. Milz, Florida, NY (US); Dan Boljonis, Middletown, NJ (US); Collin Desens, Union City, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 291 days.

This patent is subject to a terminal disclaimer.

(21) Appl. No.: 16/371,448

(22) Filed: Apr. 1, 2019

(65) Prior Publication Data
US 2019/0224025 A1 Jul. 25, 2019

Related U.S. Application Data

(63) Continuation of application No. 15/480,781, filed on Apr. 6, 2017, now Pat. No. 10,285,825.
(Continued)

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/4455* (2013.01); *A61F 2/4603* (2013.01);
(Continued)

(58) Field of Classification Search
CPC .... A61F 2/44; A61F 2/441; A61F 2/46; A61F 2/4611; A61F 2002/30537–30545;
(Continued)

(56) References Cited

U.S. PATENT DOCUMENTS 3,581,033 A 5/1971 Plumb
4,743,230 A 5/1988 Nordquest
(Continued)

FOREIGN PATENT DOCUMENTS

JP 2014500731 A 1/2014
KR 100660121 B1 12/2006
(Continued)

OTHER PUBLICATIONS

Supplementary European Search Report, dated Aug. 27, 2013, in connection with related EU10765185.3.
(Continued)

*Primary Examiner* — Eduardo C Robert
*Assistant Examiner* — Michelle C Eckman
(74) *Attorney, Agent, or Firm* — Lerner, David, Littenberg, Krumholz & Mentlik, LLP

(57) ABSTRACT

A surgical instrument includes a shaft having a distal end connectable with an implant, and a handle connected to a proximal end of the shaft. The instrument defines an internal fluid channel through which a fluid can be passed. A kit includes the instrument and a spinal implant that is expandable through the introduction of the fluid therein. A method of using the instrument includes passing a fluid through an internal fluid channel defined by the instrument and toward the implant.

20 Claims, 26 Drawing Sheets

Related U.S. Application Data

(60) Provisional application No. 62/319,460, filed on Apr. 7, 2016.

(52) U.S. Cl.
CPC .............. *A61F 2002/30579* (2013.01); *A61F 2002/30581* (2013.01); *A61F 2002/4627* (2013.01); *A61F 2002/4629* (2013.01)

(58) Field of Classification Search
CPC .. A61F 2002/30548; A61F 2002/30556; A61F 2002/30581–30588; A61B 17/885–8858
See application file for complete search history.

(56) References Cited

U.S. PATENT DOCUMENTS

| | | |
|---|---|---|
| 5,800,549 A | 9/1998 | Bao et al. |
| 5,993,416 A | 11/1999 | Choh et al. |
| 6,004,326 A | 12/1999 | Castro et al. |
| 6,167,787 B1 | 1/2001 | Jarvis |
| 6,264,659 B1 | 7/2001 | Ross et al. |
| 6,332,894 B1 | 12/2001 | Stalcup et al. |
| 6,395,007 B1 | 5/2002 | Bhatnagar et al. |
| 6,706,069 B2 | 3/2004 | Berger |
| 6,764,491 B2 | 7/2004 | Frey et al. |
| 6,796,959 B2 | 9/2004 | Davis et al. |
| 6,830,570 B1 | 12/2004 | Frey et al. |
| 6,830,574 B2 | 12/2004 | Heckele et al. |
| 7,060,073 B2 | 6/2006 | Frey et al. |
| 7,118,579 B2 | 10/2006 | Michelson |
| 7,235,082 B2 | 6/2007 | Bartish et al. |
| 7,481,812 B2 | 1/2009 | Frey et al. |
| 7,500,991 B2 | 3/2009 | Bartish, Jr. et al. |
| 7,530,970 B2 | 5/2009 | McArthur et al. |
| 7,575,580 B2 | 8/2009 | Lim et al. |
| 7,708,779 B2 | 5/2010 | Edie et al. |
| 7,799,033 B2 | 9/2010 | Assell et al. |
| 7,811,292 B2 | 10/2010 | Lo et al. |
| 7,892,239 B2 | 2/2011 | Warnick et al. |
| 7,958,804 B2 | 6/2011 | Badiali |
| 7,976,549 B2 | 7/2011 | Dye et al. |
| 7,985,256 B2 | 7/2011 | Grotz et al. |
| 7,988,695 B2 | 8/2011 | Dye |
| 8,043,293 B2 | 10/2011 | Warnick |
| 8,142,435 B2 | 3/2012 | Refai et al. |
| 8,147,554 B2 | 4/2012 | Hansell et al. |
| 8,157,845 B2 | 4/2012 | Warnick et al. |
| 8,216,317 B2 | 7/2012 | Thibodeau |
| 8,241,364 B2 | 8/2012 | Hansell et al. |
| 8,252,060 B2 | 8/2012 | Hansell et al. |
| 8,343,224 B2 | 1/2013 | Lynn et al. |
| 8,414,590 B2 | 4/2013 | Oh et al. |
| 8,419,795 B2 | 4/2013 | Sweeney |
| 8,506,636 B2 | 8/2013 | Dye |
| 8,551,172 B2 | 10/2013 | Park |
| 8,568,420 B2 | 10/2013 | O'Halloran et al. |
| 8,663,332 B1 | 3/2014 | To et al. |
| 8,690,761 B2 | 4/2014 | Begemann et al. |
| 8,753,377 B2 | 6/2014 | McCormack et al. |
| 8,998,924 B2 | 4/2015 | Simpson et al. |
| 9,060,876 B1 | 6/2015 | To et al. |
| 9,668,876 B2 | 6/2017 | Blain et al. |
| 9,681,961 B2 | 6/2017 | Prevost et al. |
| 9,808,354 B2 | 11/2017 | Willis et al. |
| 9,808,355 B2 | 11/2017 | Sweeney |
| 9,814,602 B2 | 11/2017 | Faulhaber et al. |
| 9,855,080 B2 | 1/2018 | Rabiner et al. |
| 9,987,149 B2 | 6/2018 | Simpson et al. |
| 10,285,825 B2 * | 5/2019 | Pinal ............... A61F 2/4611 |
| 2001/0021853 A1 | 9/2001 | Heckele et al. |
| 2002/0049449 A1 | 4/2002 | Bhatnagar et al. |
| 2002/0147497 A1 | 10/2002 | Belef et al. |
| 2003/0018292 A1 | 1/2003 | Kuslich et al. |
| 2004/0083002 A1 | 4/2004 | Belef et al. |
| 2004/0143283 A1 | 7/2004 | McGill et al. |
| 2004/0186576 A1 | 9/2004 | Biscup et al. |
| 2005/0113842 A1 | 5/2005 | Bertagnoli et al. |
| 2005/0131419 A1 | 6/2005 | McCord et al. |
| 2005/0209698 A1 | 9/2005 | Gordon et al. |
| 2005/0222681 A1 | 10/2005 | Richley et al. |
| 2005/0245938 A1 | 11/2005 | Kochan |
| 2006/0004326 A1 | 1/2006 | Collins et al. |
| 2006/0079898 A1 | 4/2006 | Ainsworth et al. |
| 2006/0085075 A1 | 4/2006 | McLeer |
| 2006/0155297 A1 | 7/2006 | Ainsworth et al. |
| 2006/0206209 A1 | 9/2006 | Cragg et al. |
| 2006/0235426 A1 | 10/2006 | Lim et al. |
| 2007/0093897 A1 | 4/2007 | Gerbec et al. |
| 2007/0112299 A1 | 5/2007 | Smit et al. |
| 2007/0135921 A1 | 6/2007 | Park |
| 2007/0142843 A1 | 6/2007 | Dye |
| 2007/0161962 A1 | 7/2007 | Edie et al. |
| 2007/0179614 A1 | 8/2007 | Heinz et al. |
| 2007/0191860 A1 | 8/2007 | Heinz et al. |
| 2007/0225726 A1 | 9/2007 | Dye et al. |
| 2007/0225809 A1 | 9/2007 | Ray |
| 2007/0233254 A1 * | 10/2007 | Grotz .................... A61F 2/4611 |
| | | 623/17.11 |
| 2007/0233260 A1 | 10/2007 | Cragg |
| 2008/0021563 A1 | 1/2008 | Chudzik |
| 2008/0065082 A1 | 3/2008 | Chang et al. |
| 2008/0077150 A1 | 3/2008 | Nguyen |
| 2008/0091211 A1 | 4/2008 | Gately |
| 2008/0172060 A1 | 7/2008 | Collins et al. |
| 2008/0172127 A1 | 7/2008 | Perez-Cruet et al. |
| 2008/0221694 A1 | 9/2008 | Warnick et al. |
| 2008/0262502 A1 | 10/2008 | Ainsworth et al. |
| 2008/0306557 A1 | 12/2008 | Altarac et al. |
| 2009/0043312 A1 | 2/2009 | Koulisis et al. |
| 2009/0182343 A1 * | 7/2009 | Trudeau ................ A61F 2/4657 |
| | | 606/102 |
| 2009/0240341 A1 | 9/2009 | Diwan et al. |
| 2010/0070035 A1 | 3/2010 | Mayer |
| 2010/0116360 A1 | 5/2010 | Kanner et al. |
| 2010/0262188 A1 | 10/2010 | Rabiner et al. |
| 2010/0262245 A1 | 10/2010 | Alfaro et al. |
| 2010/0305703 A1 | 12/2010 | Lin |
| 2011/0009968 A1 | 1/2011 | McCormack |
| 2011/0125158 A1 | 5/2011 | Diwan et al. |
| 2011/0130835 A1 | 6/2011 | Ashley et al. |
| 2011/0137418 A1 | 6/2011 | O'Neil et al. |
| 2011/0230970 A1 | 9/2011 | Lynn et al. |
| 2011/0257688 A1 | 10/2011 | Miller et al. |
| 2011/0257745 A1 | 10/2011 | Miller et al. |
| 2011/0276142 A1 | 11/2011 | Niemiec et al. |
| 2011/0295370 A1 | 12/2011 | Suh et al. |
| 2012/0041557 A1 | 2/2012 | Frigg |
| 2012/0065613 A1 | 3/2012 | Pepper et al. |
| 2012/0067204 A1 * | 3/2012 | Kanner ........... A61M 25/10182 |
| | | 92/5 L |
| 2012/0101576 A1 | 4/2012 | Dewey et al. |
| 2012/0101577 A1 | 4/2012 | Lee |
| 2012/0130387 A1 * | 5/2012 | Simpson ............... A61F 2/4611 |
| | | 606/104 |
| 2012/0136315 A1 | 5/2012 | Wieselblad et al. |
| 2012/0150241 A1 | 6/2012 | Ragab et al. |
| 2012/0265304 A1 | 10/2012 | Mayer |
| 2013/0006365 A1 | 1/2013 | Pepper et al. |
| 2013/0190875 A1 | 7/2013 | Shulock et al. |
| 2014/0005630 A1 | 1/2014 | Bagaoisan et al. |
| 2014/0107789 A1 | 4/2014 | Schaller et al. |
| 2014/0180415 A1 | 6/2014 | Koss |
| 2015/0112437 A1 | 4/2015 | Davis et al. |
| 2015/0190242 A1 | 7/2015 | Blain et al. |
| 2015/0351925 A1 | 12/2015 | Emerick et al. |
| 2016/0030195 A1 | 2/2016 | Prevost et al. |
| 2016/0058575 A1 | 3/2016 | Sutterlin, III et al. |
| 2016/0113776 A1 | 4/2016 | Capote |
| 2016/0120653 A1 | 5/2016 | Hibri et al. |
| 2016/0242823 A1 | 8/2016 | Perez-Cruet et al. |
| 2016/0278822 A1 | 9/2016 | Davis et al. |
| 2016/0296344 A1 | 10/2016 | Greenhalgh et al. |
| 2016/0317324 A1 | 11/2016 | Cho et al. |

(56) References Cited

U.S. PATENT DOCUMENTS

| | | |
|---|---|---|
| 2016/0331542 A1 | 11/2016 | Faulhaber et al. |
| 2017/0056195 A1 | 3/2017 | Lutz et al. |
| 2017/0071753 A1 | 3/2017 | Josse et al. |
| 2017/0196702 A1 | 7/2017 | Agarwal et al. |
| 2017/0216044 A1 | 8/2017 | McCormack |
| 2017/0224484 A1 | 8/2017 | Pintor et al. |
| 2017/0258605 A1 | 9/2017 | Blain et al. |
| 2017/0319352 A1 | 11/2017 | Dewey et al. |
| 2017/0333199 A1 | 11/2017 | Sharifi-Mehr et al. |
| 2017/0340358 A1 | 11/2017 | Bullard |
| 2017/0348115 A1 | 12/2017 | Greenhalgh et al. |
| 2018/0014944 A1 | 1/2018 | Davis et al. |
| 2018/0021148 A1 | 1/2018 | Baynham |

FOREIGN PATENT DOCUMENTS

| | | |
|---|---|---|
| WO | 9531948 A1 | 11/1995 |
| WO | 2002017823 A1 | 3/2002 |
| WO | 2008041972 A2 | 4/2008 |
| WO | 2008131498 A1 | 11/2008 |
| WO | 2012021148 A1 | 2/2012 |

OTHER PUBLICATIONS

International Search Report and Written Opinion dated Nov. 11, 2010 in relation International Application No. PCT/US2010/031247.

Extended European Search Report for Application No. 15189369.0 dated May 4, 2016.

Stryker, AccuLIF, Expandable TLIF and PLIF Technology, Surgical Technique Guide, Copyright 2015, pp. 1-48.

Extended European Search Report for Application No. 17165366.0 dated Aug. 29, 2017.

* cited by examiner

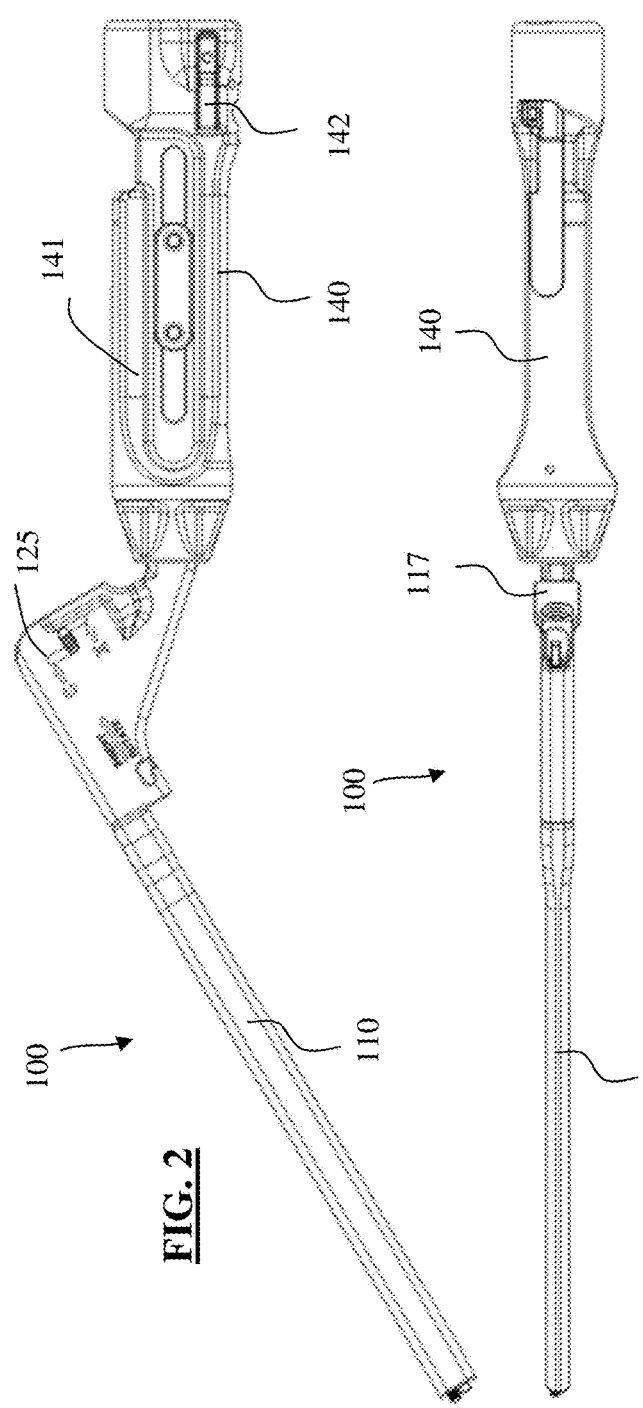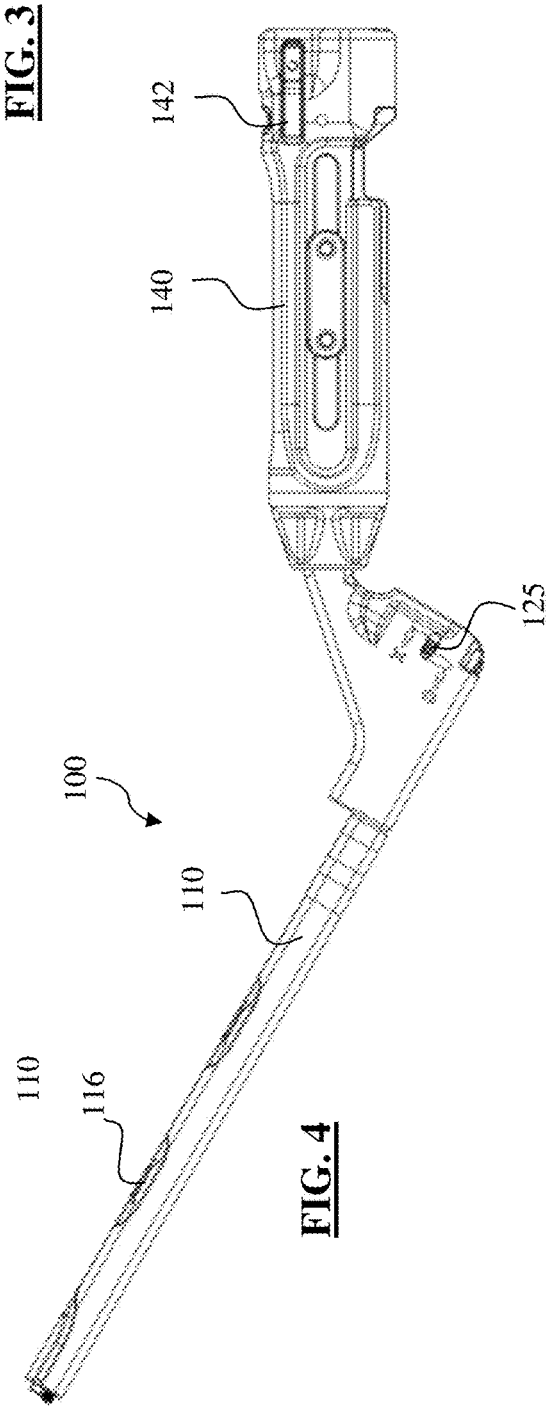

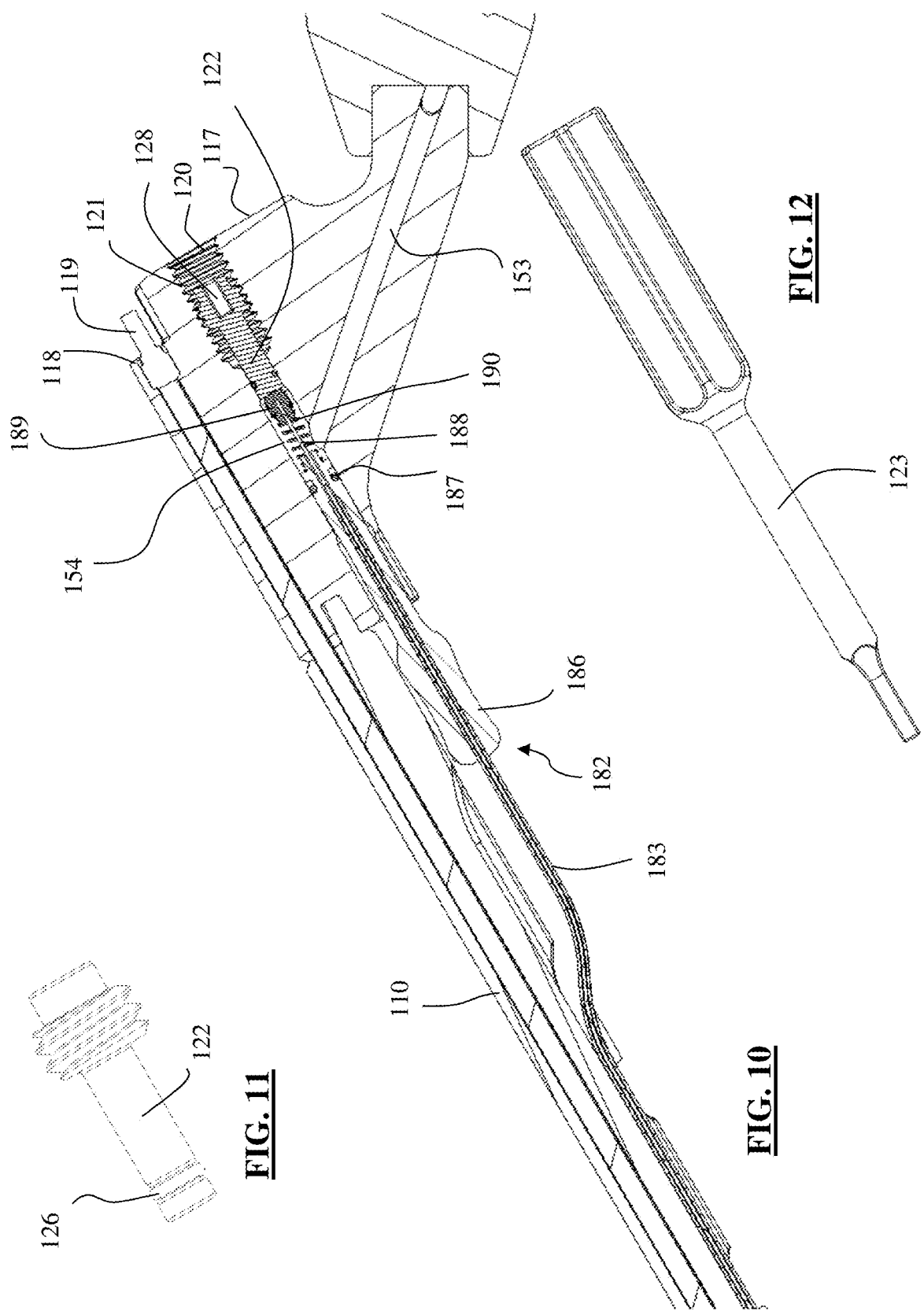

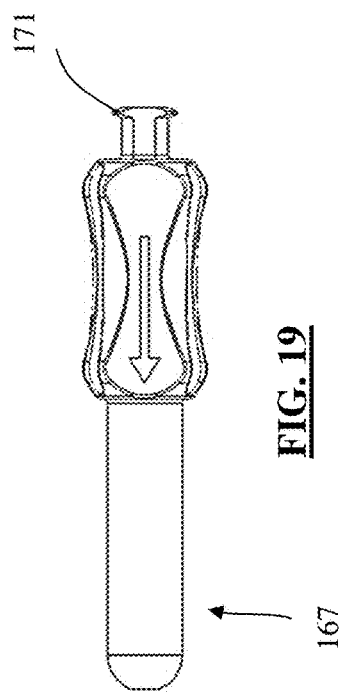
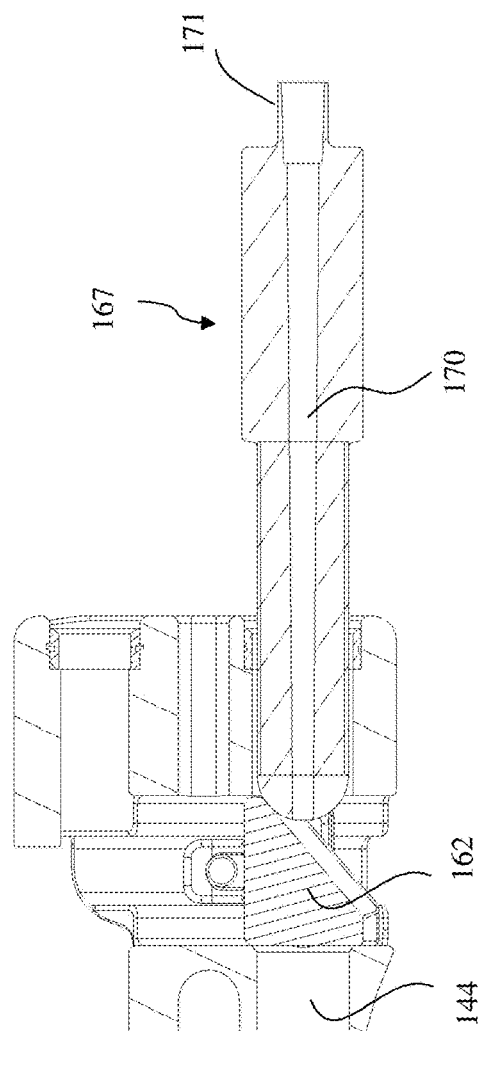
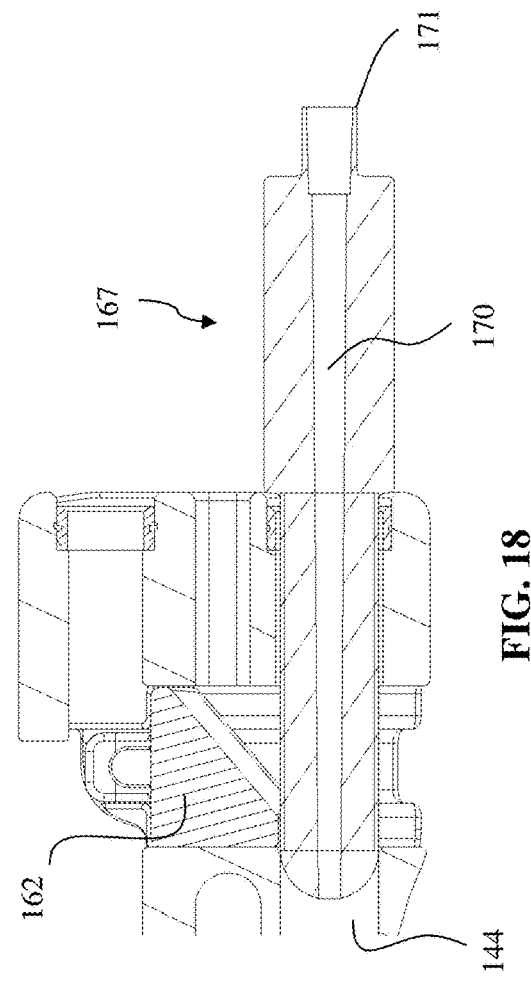
FIG. 19
FIG. 17
FIG. 18

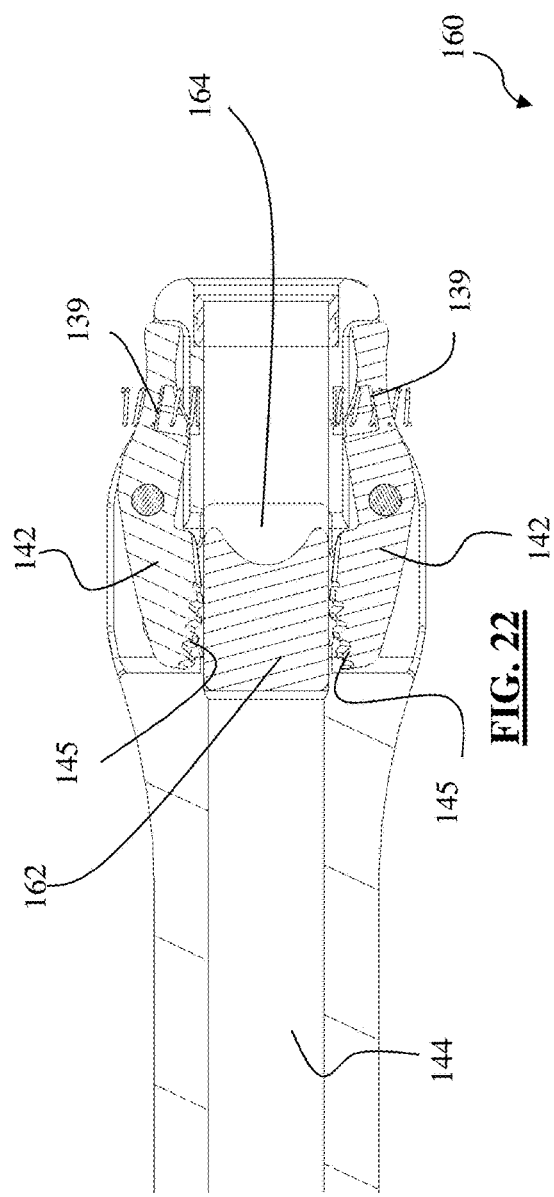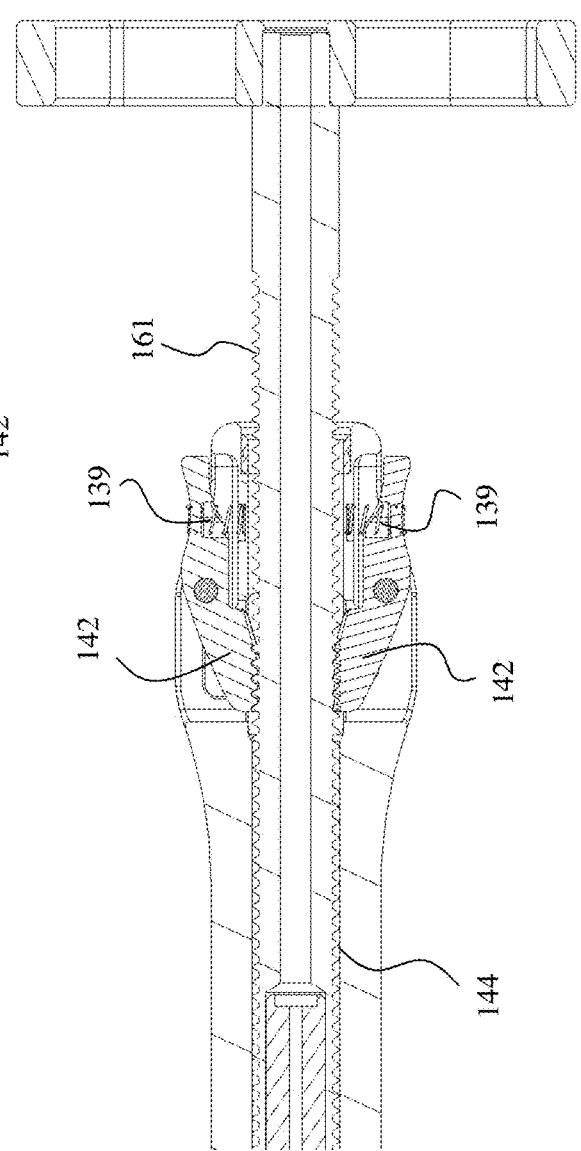

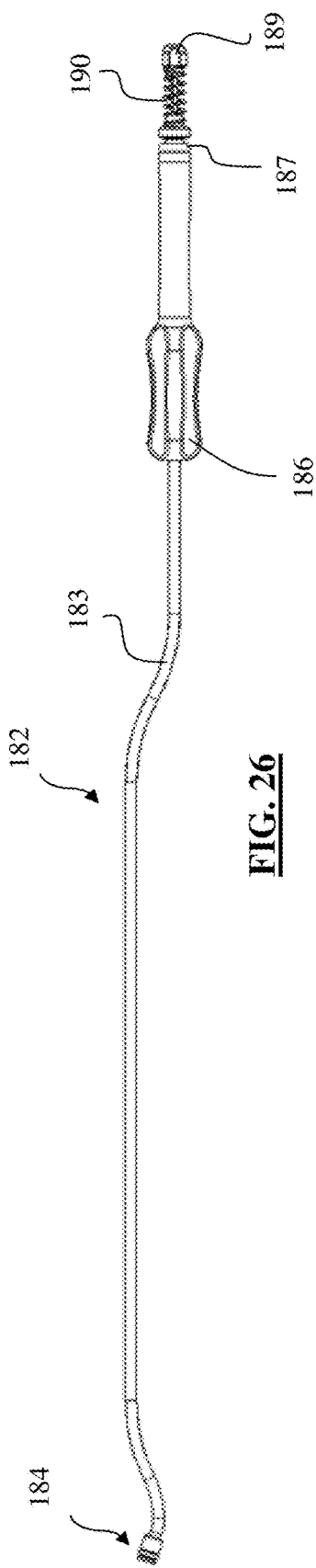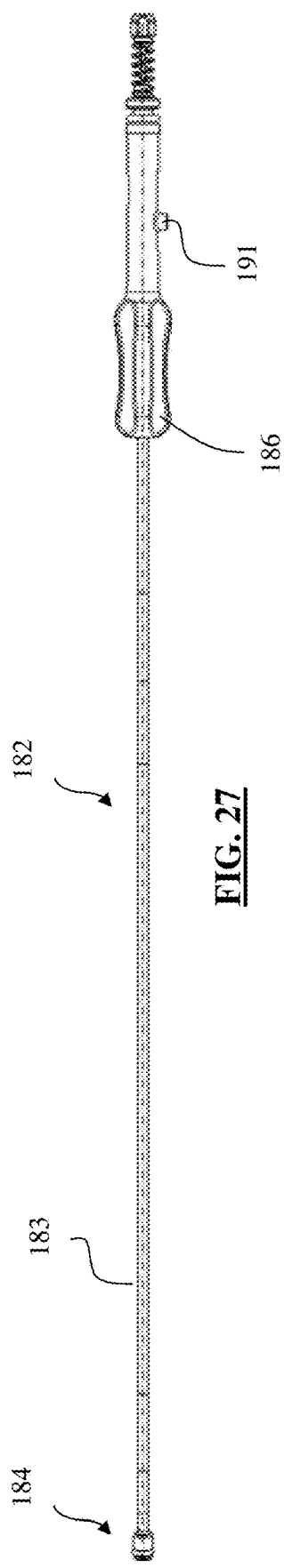

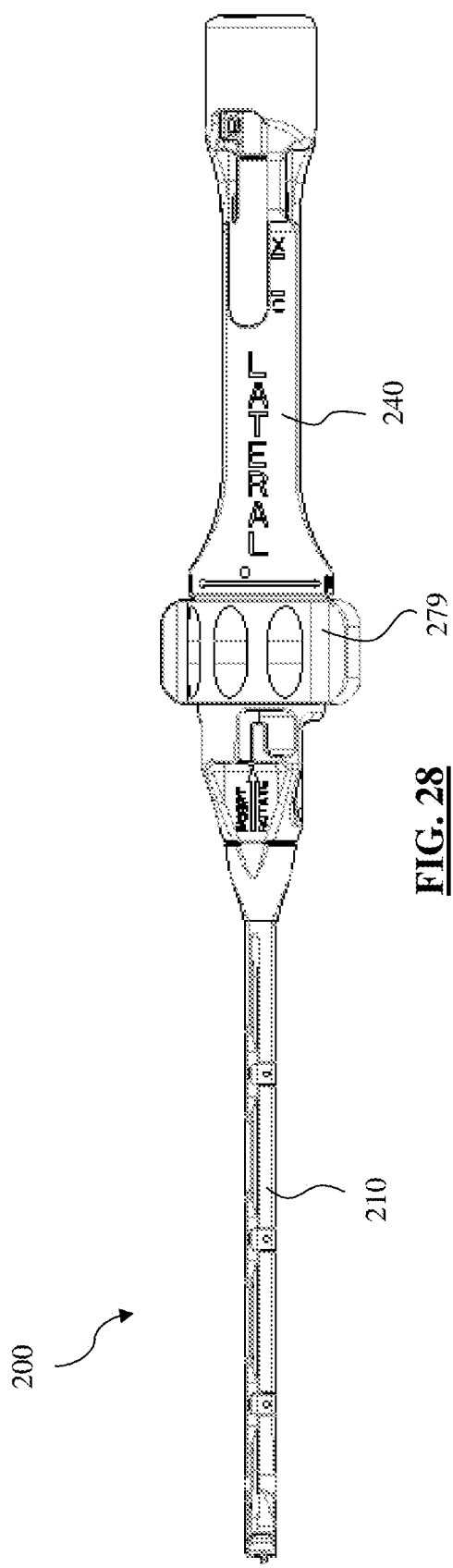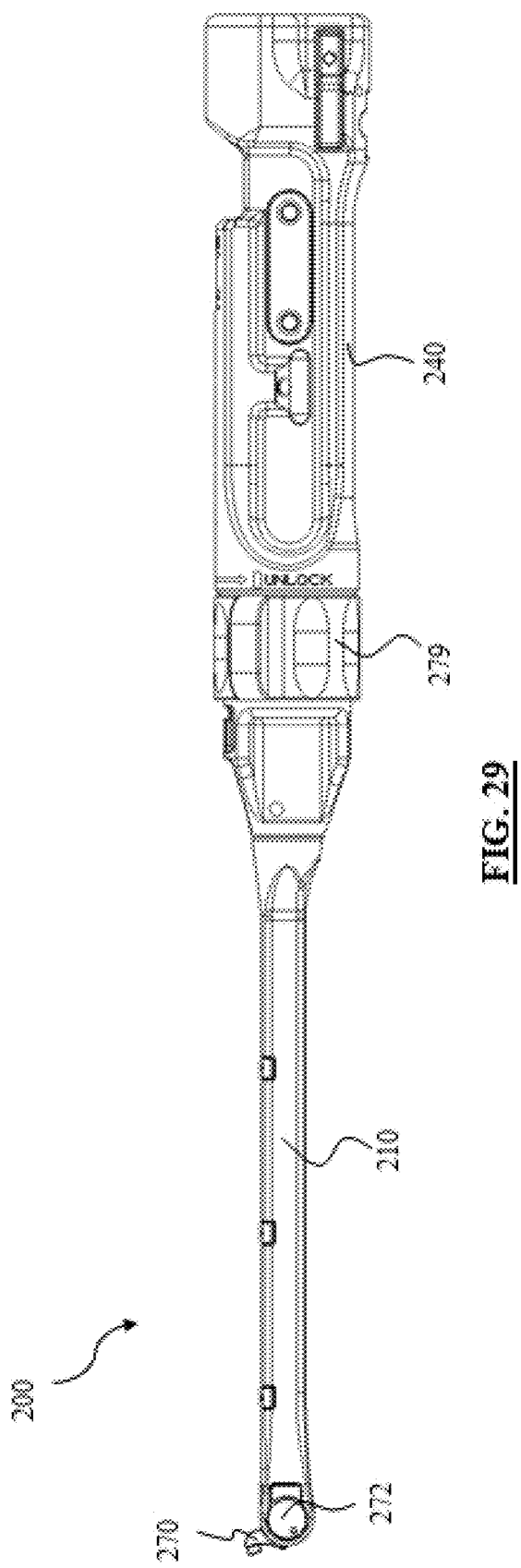
FIG. 28
FIG. 29

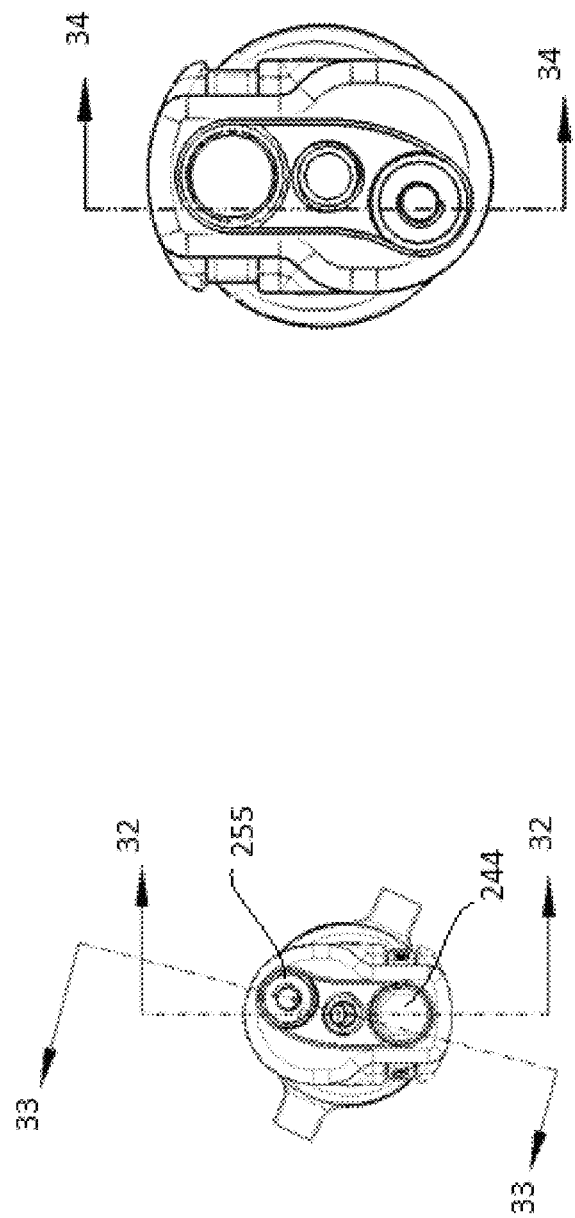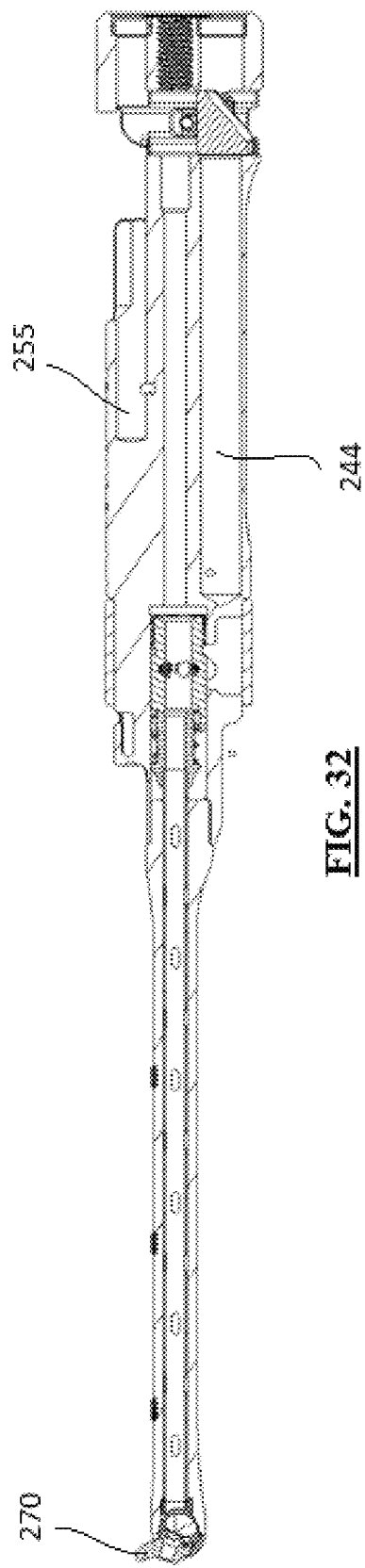
FIG. 31
FIG. 32
FIG. 30

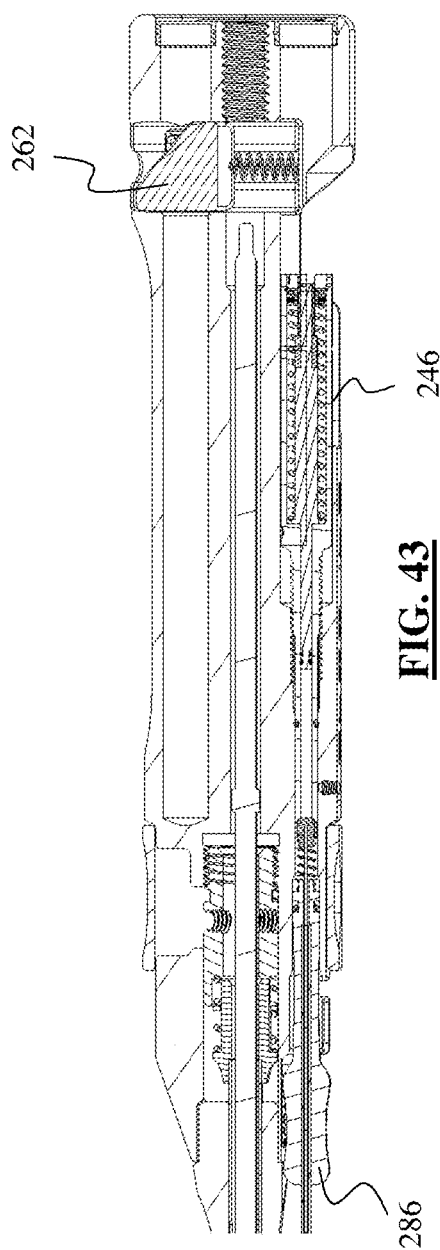
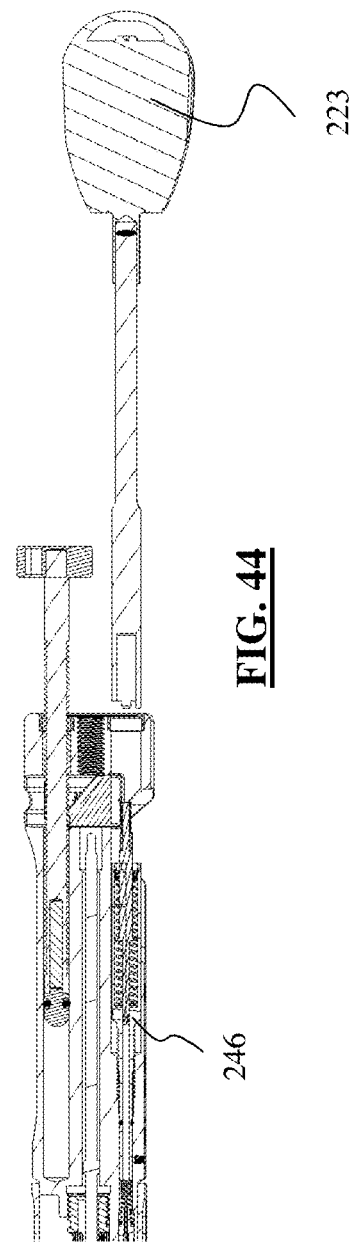
FIG. 43
FIG. 44

SURGICAL INSERTION INSTRUMENTS

CROSS-REFERENCE TO RELATED APPLICATIONS

The present application is a continuation of U.S. patent application Ser. No. 15/480,781, filed on Apr. 6, 2017, which claims the benefit of the filing date of U.S. Provisional Patent Application No. 62/319,460 filed Apr. 7, 2016, the disclosures of which are hereby incorporated herein by reference.

BACKGROUND OF THE INVENTION

The present inventions relate to surgical instruments used during the insertion of spinal implants and methods of using such instruments. More particularly, the present inventions relate to instruments capable of passing a fluid through an internal fluid channel thereof and into an implant to cause expansion of the implant.

Intervertebral implants are commonly used in spinal surgery, such as in interbody fusion procedures, in which an implant (e.g., a spacer or cage) is placed in the disc space between two vertebrae to be fused together. At least a portion of the disc is typically removed before the implant is positioned in the intervertebral space, and the implant may be supplemented with bone graft material to promote fusion of the vertebrae. Interbody fusion procedures may also be performed in conjunction with other types of fixation, such as pedicle screw fixation, to provide additional stability, particularly while the vertebrae fuse together.

Different interbody fusion procedures can be distinguished by their location along the spine (e.g., in the cervical, thoracic, or lumbar regions); by the type of implant used; and by the surgical approach to the intervertebral space, in which different surgical approaches often imply different structural characteristics of the implant or implants used. Different surgical approaches to the spine include anterior, posterior, and lateral. Examples of interbody fusion techniques performed along a posterior approach include posterior lumbar interbody fusion (PLIF) and transforaminal lumbar interbody fusion (TLIF). PLIF techniques typically include positioning two intervertebral implants into the intervertebral space along a posterior to anterior direction, with one implant being positioned towards the left side of the spine and one implant being positioned towards the right side of the spine. The implants used in such PLIF techniques typically have a straight shape, in that they extend along a central axis. TLIF techniques, by contrast, typically include positioning one intervertebral implant into the intervertebral space (often towards the anterior portion of the intervertebral space) from the posterior of the patient, but the spine is approached on one side from a more lateral position than in PLIF techniques. The implants used in such TLIF techniques are often curved, such that they have an overall kidney bean-like shape.

Included among the different types of intervertebral implants are expandable implants. Such implants often have an initially contracted configuration, such that they have a low profile in the superior-inferior direction, in order to ease insertion into the intervertebral space. Such expandable implants can then be expanded in the superior-inferior direction after implantation, so as to securely engage and stabilize the vertebrae on both sides of the intervertebral space. Examples of such expandable intervertebral implants are disclosed in U.S. Pat. No. 8,992,620, which is hereby incorporated by reference herein as if fully set forth herein.

Insertion of an expandable implant requires one or more instruments capable of inserting an implant to its final destination within the disc space, typically based on one of the aforementioned approaches, and expanding the implant during or after insertion. Examples of such instruments are disclosed in U.S. Pat. No. 8,998,924, which is hereby incorporated by reference herein as if fully set forth herein.

Although considerable effort has been devoted in the art to optimization of such instruments and methods, still further improvement is desirable.

BRIEF SUMMARY OF THE INVENTION

A first aspect of the present invention is a surgical instrument including a shaft having a distal end connectable with an implant, and a handle connected to a proximal end of the shaft, wherein the instrument defines an internal fluid channel through which a fluid can be passed.

In accordance with other embodiments of the first aspect, the internal fluid channel may include a cavity in the handle, and the handle may include an aperture in a proximal portion of the handle that is in communication with the cavity. The handle may include a movable valve configured to seal the cavity at the aperture. The surgical instrument may further include a plunger movable within the cavity to force fluid from the aperture to a distal portion of the cavity. The plunger may have an externally threaded section. The handle may include a toggle having an internally threaded section configured to selectively engage the externally threaded section of the plunger. When the toggle is in an engaged position, the plunger may only move within the cavity by rotating the plunger to engage the externally threaded section of the plunger with the internally threaded section of the toggle. When the toggle is in a disengaged position, the plunger may move freely within the cavity. The toggle may include opposing first and second toggle clips. The toggle clips may be spring biased to the engaged position.

The surgical instrument may further include a tubular duct having a proximal end configured to connect to the instrument to communicate with the internal fluid channel and a distal end configured to connect to the distal end of the shaft to allow passage of a fluid from the internal fluid channel to the implant. The proximal end of the tubular duct may be at least partially disposed within a passage of the handle. The shaft may include a recessed passage in which a portion of the tubular duct can be disposed. The tubular duct may be configured to move along the shaft within the recessed passage. The proximal end of the tubular duct may be at least partially disposed within a passage of the shaft. The tubular duct may include a wire disposed within a tube, wherein the wire is movable between a proximal position and a distal position, the wire being configured to cooperate with a mechanism of the implant when in the distal position. The wire may be spring biased to the proximal position. The surgical instrument may further include a gauge in communication with the fluid channel and configured to indicate pressure within the fluid channel, wherein the gauge is movable within a gauge cavity in the handle and can be advanced to move the wire from the proximal position to the distal position. The surgical instrument may further include a collapse shaft movable within a cavity in the handle, wherein the collapse shaft can be advanced to move the wire from the proximal position to the distal position.

The surgical instrument may further include a gauge in communication with the fluid channel and configured to indicate pressure within the fluid channel. The handle may extend along an axis that is angled with respect to an axis along which the shaft extends. The surgical instrument may further include a rod disposed within at least a portion of the shaft and having a threaded distal end for attaching to the implant.

A second aspect of the present invention is a kit including a spinal implant and a surgical instrument including a shaft having a distal end connectable with an implant, and a handle connected to a proximal end of the shaft, wherein the instrument defines an internal fluid channel through which a fluid can be passed. In accordance with another embodiment of the second aspect, the spinal implant may be expandable through the introduction of the fluid therein.

A third aspect of the present invention is a method of using a surgical instrument including steps of connecting an implant to a distal end of a shaft of the instrument, the instrument including a handle connected to a proximal end of the shaft, and passing a fluid through an internal fluid channel defined by the instrument and toward the implant.

In accordance with other embodiments of the third aspect, the method may further include a step of loading the fluid into a cavity of the internal fluid channel that is disposed in the handle. The step of loading the fluid may include introducing the fluid through an aperture of the handle that is in communication with the cavity. The step of loading may further include moving a valve of the handle away from the aperture. The method may further include a step of advancing a plunger within a cavity of the internal fluid channel that is disposed in the handle to force the fluid distally in the cavity. The step of advancing may include threading the plunger into the cavity. The step of advancing may further include engaging an externally threaded section of the plunger with an internally threaded section of a toggle of the handle. The method may further include a step of actuating the toggle to a disengaged position so that the internally threaded section is not in communication with the externally threaded section of the plunger and the plunger can move freely within the cavity.

The method may further include steps of connecting a proximal end of a tubular duct to the instrument and into communication with the internal fluid channel, and connecting a distal end of the tubular duct to the distal end of the shaft, wherein the tubular duct allows passage of the fluid from the internal fluid channel to the implant. The method may further include a step of passing the fluid through the internal fluid channel, through the tubular duct, and into the implant to expand the implant. The step of connecting the proximal end of the tubular duct may include placing at least a part of the proximal end within a passage of the handle. The method may further include a step of placing a portion of the tubular duct in a recessed passage of the shaft. The method may further include a step of allowing the tubular duct to move along the shaft within the recessed passage. The step of connecting the proximal end of the tubular duct may include placing at least a part of the proximal end within a passage of the shaft. The method may further include a step of advancing a wire disposed within a tube of the tubular duct to a distal position to cooperate with a mechanism of the implant. The step of advancing the wire may cause the implant to reduce in size. The step of advancing the wire may include advancing a gauge in communication with the fluid channel to indicate pressure within the fluid channel to move the wire to the distal position. The step of advancing the wire may include advancing a collapse shaft to move the wire to the distal position. The method may further include a step of threading a rod disposed within at least a portion of the shaft to attach a threaded distal end of the rod to the implant.

BRIEF DESCRIPTION OF THE DRAWINGS

FIGS. 2-4 are a first side elevational view, a top view, and a second side elevational view, respectively, of the instrument shown in FIG. 1.

FIG. 10 is a side sectional view of a portion of the instrument shown in FIG. 1.

FIG. 11 is a side elevational view of an implant collapse shaft of the instrument shown in FIG. 1.

FIG. 12 is a side elevational view of a driver of the instrument shown in FIG. 1.

FIGS. 17 and 18 are side sectional views of the handle of the instrument shown in FIG. 1 used with a syringe extension.

FIG. 19 is a side elevational view of the syringe extension shown in FIG. 17.

FIG. 22 is a bottom sectional view of a proximal portion of the handle of the instrument shown in FIG. 1.

FIG. 23 is a bottom sectional view of a proximal portion of the handle of the instrument shown in FIG. 1 used with a plunger.

FIGS. 26 and 27 are side and top elevational views, respectively, of a tube set of the instrument shown in FIG. 1.

FIGS. 28 and 29 are side and top elevational views, respectively, of a surgical instrument including in accordance with another embodiment of the present invention.

FIG. 30 is a rear view of the instrument shown in FIG. 28.

FIG. 31 is a rear view of just the handle of the instrument shown in FIG. 28.

FIG. 32 is a side sectional view of the instrument shown in FIG. 28 taken along the line 32-32 of FIG. 30.

FIG. 43 is a side sectional view of a proximal portion of the handle of the instrument shown in FIG. 28.

FIG. 44 is a side sectional view of a proximal portion of the handle of the instrument shown in FIG. 28 used with a plunger and a driver.

DETAILED DESCRIPTION

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents that operate in a similar manner to accomplish similar purpose.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
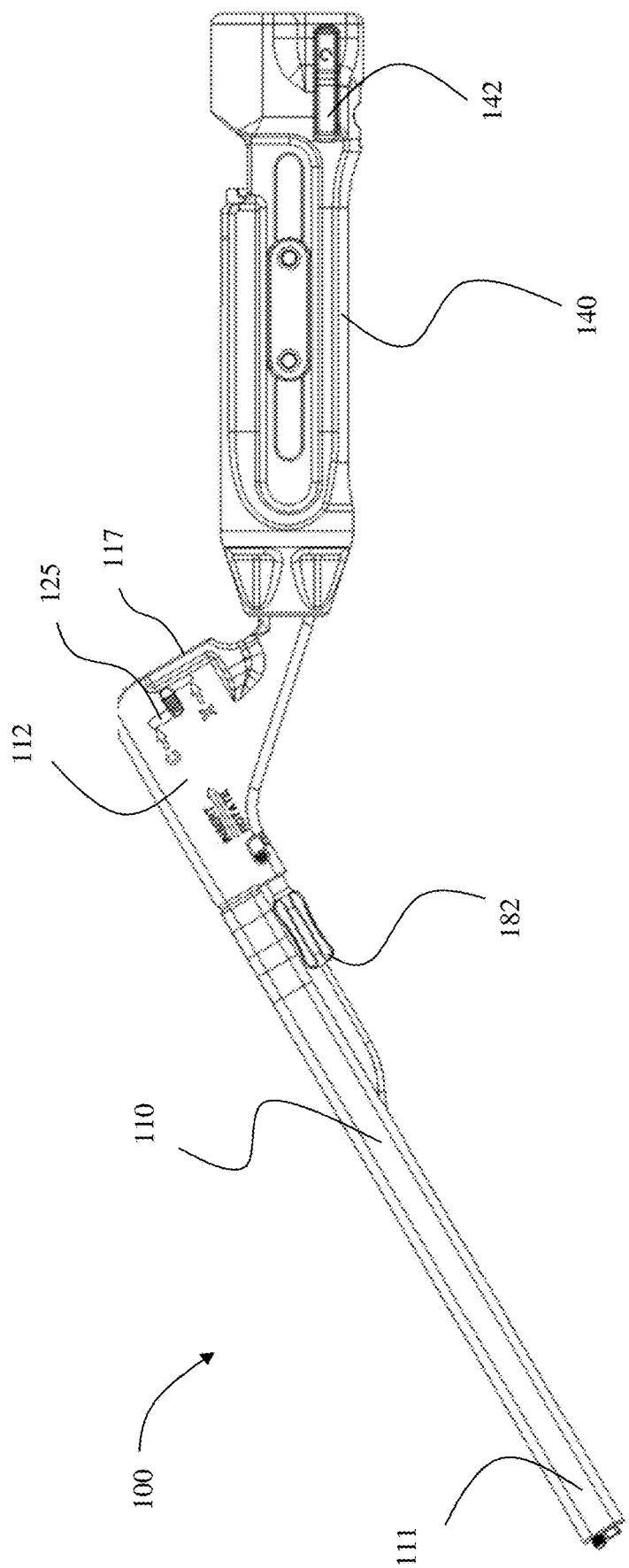
FIG. 1 is a side elevational view of a surgical instrument including a tube set in accordance with one embodiment of the present invention.
Figure 5:
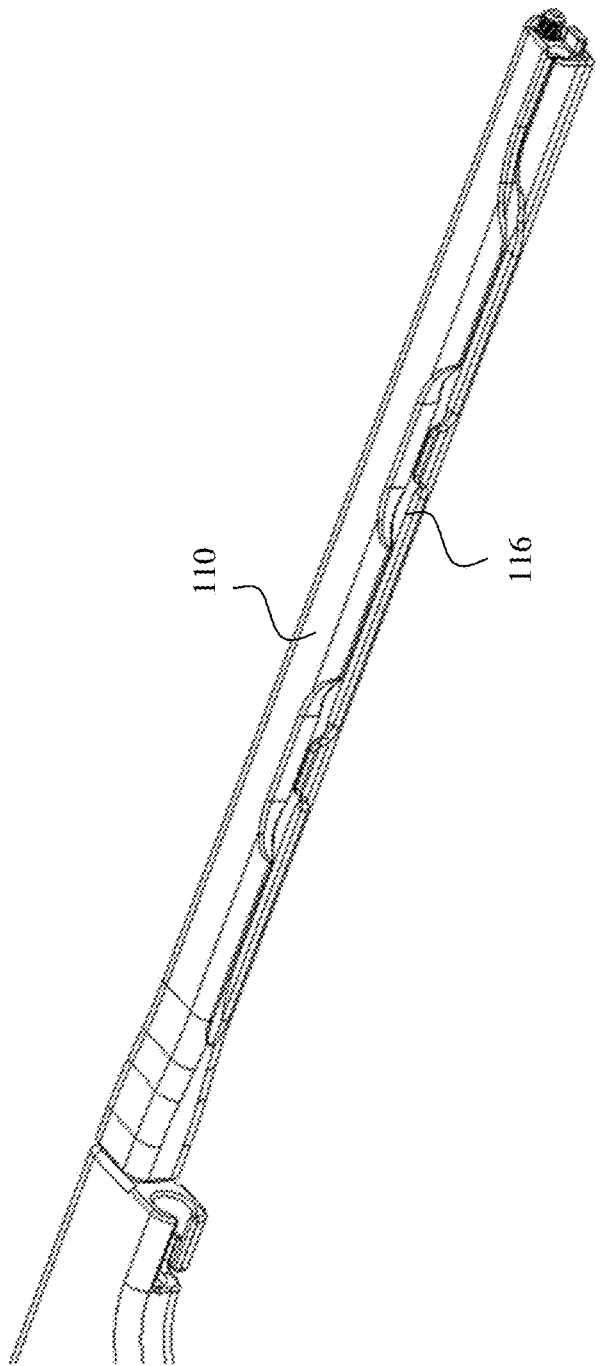
FIG. 5 is a front perspective view of a shaft of the instrument shown in FIG. 1.
Figure 7:
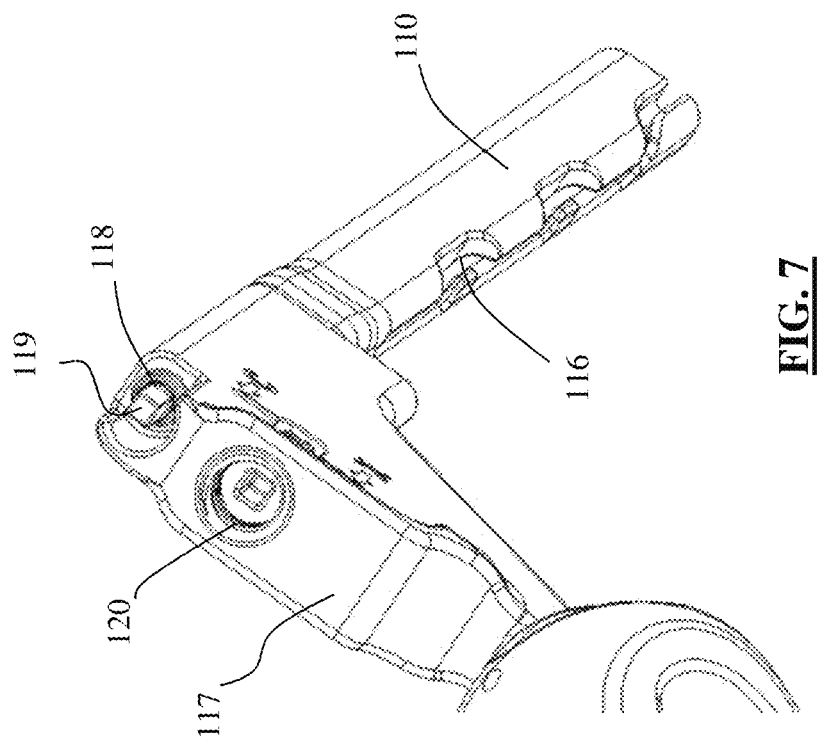
FIG. 7 is a rear perspective view of the shaft of the instrument shown in FIG. 1.
Figure 6:
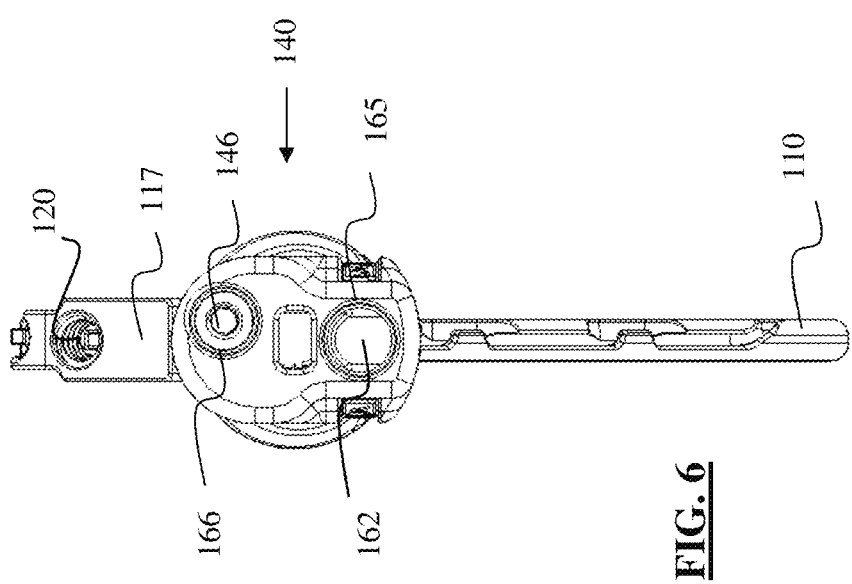
FIG. 6 is a rear view of the instrument shown in FIG. 1.

A first embodiment of a surgical instrument 100 is depicted in FIGS. 1-26. Instrument 100 is bayoneted such that it includes a shaft 110 that extends along an axis that is angled with respect to an axis along which a handle 140 extends, as shown in FIGS. 1, 2, and 4. This allows for the distal portion of instrument 100 to be utilized at a surgical site while handle 140 is disposed outside of the direct line of site of the distal portion while in use to improve visualization through an access instrument, such as a retractor or tube used in MIS procedures. The bayoneted configuration of instrument 100 allows for the length of shaft 110 to be offset from handle 140 and aid in visualization. It also allows room for an impaction surface 117 on the proximal end of a proximal portion 112 of shaft 110 if the user desires a more inline impaction than that provided on the back of handle 140, as shown in FIGS. 6 and 7.

As shown more clearly in FIGS. 1-4, a distal portion 111 of shaft is monolithically constructed with the rest of shaft 110. Distal portion 111 of shaft 110 has a face 113 from which a threaded rod 114 of a draw rod 119 protrudes. Rod 114 can be engaged with a threaded hole of a surgical implant to secure such implant to instrument 100 at face 113. Such a surgical implant is shown and described in U.S. Provisional Patent Application No. 62/319,513 filed on Apr. 7, 2016, entitled Expandable Interbody Implant, the disclosure of which is hereby incorporated by reference herein as if fully set forth herein. An anti-rotation feature 115 also protrudes from face 113 and is dimensioned to mate with a corresponding feature of the surgical implant to prevent rotation and maintain a substantially static connection between instrument 100 and the surgical implant during a surgical procedure. Flanges 127 are disposed on either side of face 113 to more accurately match the curve of the implant to make the connection flush.

Figure 9:
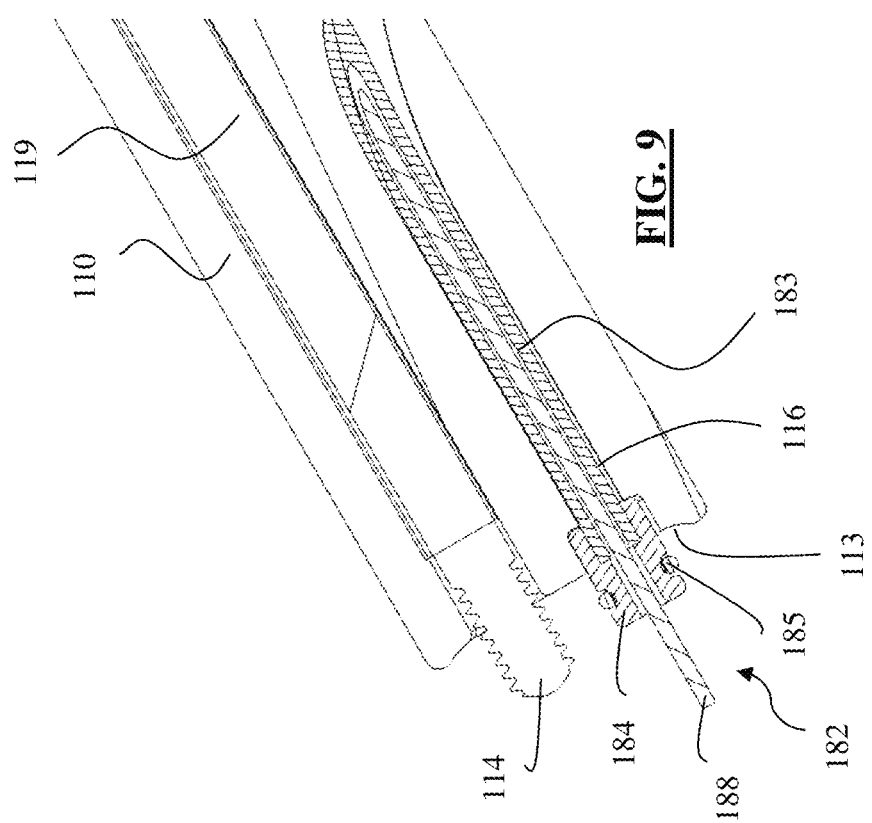
FIG. 9 is a side sectional view of a distal end of the shaft of the instrument shown in FIG. 1.

A tube set 182 is shown connected with instrument 100 in FIGS. 1, 9, and 10. Tube set 182, which is depicted alone in FIGS. 26-28, is the duct or conduit through which saline is passed from handle 140 to the surgical implant. It includes a flexible tube 183, a distal exit port 184 with an o-ring 185 or seal, and a proximal attachable end 186 having an o-ring 187 or seal. Proximal attachable end 186 can be loaded into a port in shaft 110 such that the aspects of tube set 182 located proximally of o-ring 187 are in communication with the saline delivery system within shaft 110 and handle 140. Tube set 182 further includes an unlock wire 188 made of nitinol and having a proximal knob 189, which is separated from a proximal end of proximal attachable end 186 via a spring 190. The contours of knob 189 and the open areas of spring 190 allow saline to pass through or around them to enter and travel through flexible tube 183. The dimensions of unlock wire 188 are such that saline can flow around and past unlock wire 188 within flexible tube 183 to ultimately flow out of distal exit port 184 and into a connected implant.

Figure 8:
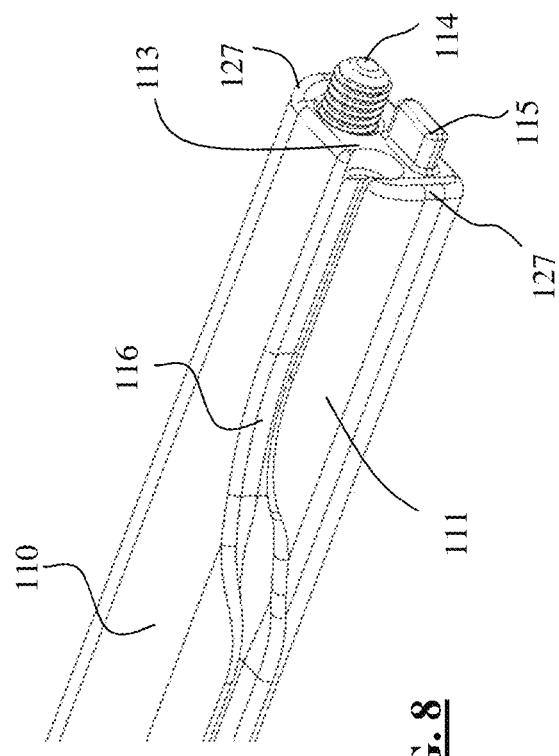
FIG. 8 is a front perspective view of a distal end of the shaft of the instrument shown in FIG. 1.

As shown in FIG. 9, distal exit port 184 is configured to be attached within distal end 111 of shaft 110 so that it is positioned to engage a portal of the surgical implant. More specifically, as shown in FIG. 8, tube set 182 is located within a recessed passage 116 of shaft 110 so that distal exit port 184 is exposed at face 113 of distal portion 111 of shaft 110. O-ring 185 of tube set 182 allows for a sealed connection with the implant. Unlock wire 188 extends through distal exit port 184. Distal movement of knob 189 of unlock wire 188 causes distal movement of unlock wire 188 within flexible tube 183 so that it can cooperate with a mechanism of the implant to collapse the implant, as explained further below. In its resting state, spring 190 can maintain unlock wire 188 in a proximal position. Spring 190 provides resistance when moving unlock wire 188 distally.

As shown in FIG. 7, at a proximal end of proximal portion 112 of shaft 110, an aperture 118 provides access to the proximal end of draw rod 119, which is connected with threaded rod 114. The proximal end of draw rod 119 includes a non-circular head through which a corresponding instrument can be used to rotate draw rod 119 along its axis, which actuates threaded rod 114 to engage the surgical implant. The configuration of the proximal end of draw rod 119 can be a square head (as shown), a hex head, or the like. Draw rod 119 is preferably removably positioned within shaft 111 and monolithically connected with threaded rod 114.

Also at a proximal end of proximal portion 112 of shaft 110, an aperture 120 provides access to unlock wire 188 of tube set 182. Aperture 120 includes an internal threaded portion 121 that can cooperate with external threads on an implant collapse shaft 122, shown in FIGS. 10 and 11. Implant collapse shaft 122 can be advanced distally within aperture 120 via engagement by a driver 123, shown in FIG. 12, in a non-circular driver keyway 128 of implant collapse shaft 122. When advanced, a distal end of implant collapse shaft 122 engages knob 189 of tube set 182 to advance unlock wire 188 distally. Through rotation, the threads allow for advancing and retracting unlock wire 188 in a more precise manner. The engagement between implant collapse shaft 122 and driver 123 can be a hex head, square head, or the like. Threaded portion 121 of aperture 120 can also be connected with a slap hammer or strike plate to assist with inserting or removing an attached implant with respect to the intervertebral space. A distal end of threaded portion 121 provides a depth stop for inserting implant collapse shaft 122 only to a particular depth. Implant collapse shaft 122 also has an o-ring 126 at a distal end thereof to prevent backflow of saline and to maintain a seal in the internal passage system of instrument 100, which is described further below.

As shown in FIGS. 2 and 4, windows 125 on both sides of shaft 110 can reveal a position of implant collapse shaft 122 to identify its location within shaft. A mark denoted with a "C" located at a distal end of window 125 is aligned with the proximal end of implant collapse shaft 122 when unlock wire 188 is in position to collapse the surgical implant. A mark denoted with an "X" located at a proximal end of window 125 is aligned with the proximal end of implant collapse shaft 122 when unlock wire 188 is in position to allow expansion of the surgical implant. Alternately, different identifiers may be used for expanded and collapsed positions, and other positions could be identified as well.

Draw rod 119 and tube set 182 provide a dual shaft system in that they run in parallel down the length of shaft 110, as shown in FIGS. 9 and 10. Draw rod 119 is offset from the saline delivery line in which tube set 182 is disposed to allow for optimal wall thickness and strength throughout the instrument 100. Draw rod 119 is recessed below an impaction surface 117 at a proximal end of shaft 110.

Handle 140 is rigidly connectable with proximal portion 112 of shaft 110. This connection can be permanent or removable, though it is configured to be rigidly maintained during a surgical procedure. Instrument 100 utilizes a rigid threaded connection which provides the user a stable and consistent means of insertion. The rigid connection also allows for a more reliable seal between the implant and the instrument 100. In removable configurations of instrument 100, some components can be sterilized such as by autoclaving and reused with new versions of other replaceable components.

Handle 140 includes a grip portion 141 at which a user can hold handle 140. As shown in FIGS. 1, 2, 4, 22, and 23, a toggle 142 is a two-piece structure located at a proximal end of handle 140 and is used to engage and disengage a syringe plunger 160, shown in FIGS. 20-25. Toggle 142 communicates with a cylindrical cavity 144 within handle 140. Plunger 160 extends into cylindrical cavity 144 of handle 140 and can be contacted by threaded inner surfaces 145 of toggle 142. Toggle 142 can move between an engaged position (shown in FIG. 23) and a disengaged position (shown in FIG. 22). In the engaged position, the threaded inner section 145 toggle 142 engages an externally threaded section including threads 161 of plunger 160. In this engaged position, plunger 160 can only move within cylindrical cavity 144 by being rotated to advance or retract it. In the disengaged position, the inner surfaces 141 of toggle 142 are disengaged from threads 161, allowing plunger 160 to move freely to be advanced or retracted within cylindrical cavity 144 simply due to force applied to plunger 160 along its axis. This allows for a more rapid insertion and release of plunger 160 within cylindrical cavity 144. Toggle 142 includes two toggle clips, one on each side of handle 140. The toggle clips can be moved by simply pushing proximal surfaces thereof, which pivots the threaded inner surfaces 145 away from each other. Toggle 142 is maintained in its engaged position by springs 139.

Cylindrical cavity 144 of handle 140 is part of an internally fluid channel of instrument 100 that is configured to hold saline or another fluid, which can be passed through instrument 100 into the surgical implant to facilitate expansion of the implant. Plunger 160 is the mechanism by which the saline is forced toward the surgical implant. Care must be taken while expanding the implant within an intervertebral disc space so as not to cause trauma to the patient. With this in mind, rotation of plunger 160 when toggle 142 is in its engaged position allows for precisely controlled translation of plunger 160 within cylindrical cavity 144, which therefore allows for a precisely controlled amount of saline to be displaced toward the implant. When needed, toggle 142 can be moved to its disengaged position to allow for a more rapid insertion of saline, or for a more rapid removal of plunger 160 after a surgical procedure. Plunger 160 includes an integrated pressure relief valve to provide pressure relief when the pressure exceeds a certain value, such as 2000 psi. Under those circumstances, plunger 160 bleeds out any air or saline in the system. Also, when disengaged from the implant, unlock wire 188 can be translated distally to a location in which its distal end plugs distal exit port 184 to prevent leakage of saline from the system.

Figure 20:
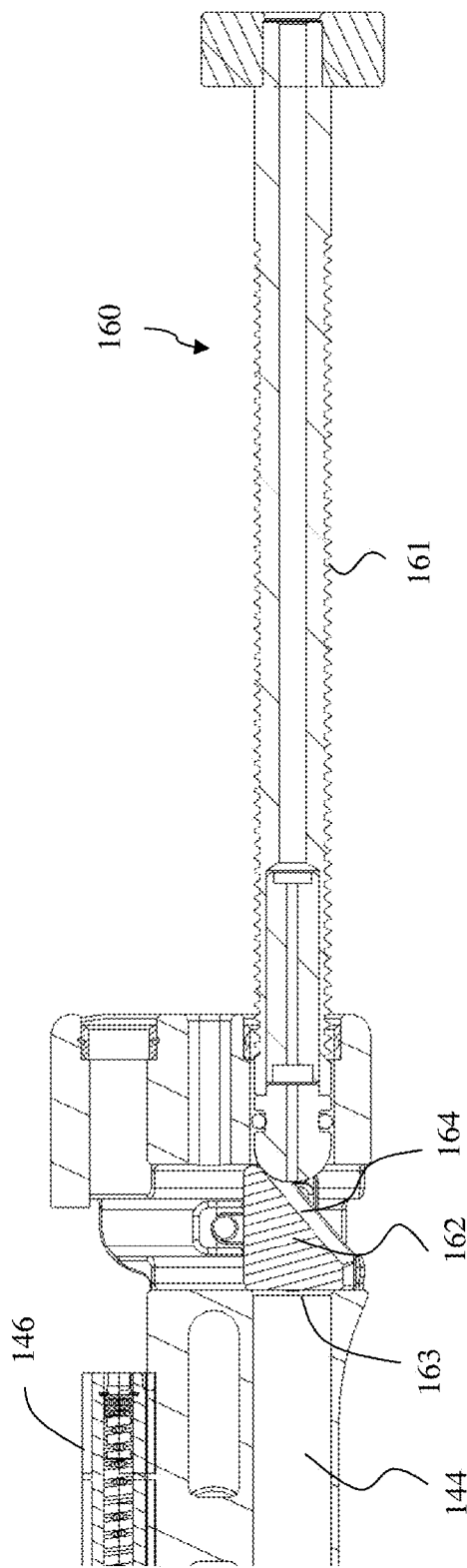
FIGS. 20 and 21 are side sectional views of a proximal portion of the handle of the instrument shown in FIG. 1 used with a plunger.
Figure 21:
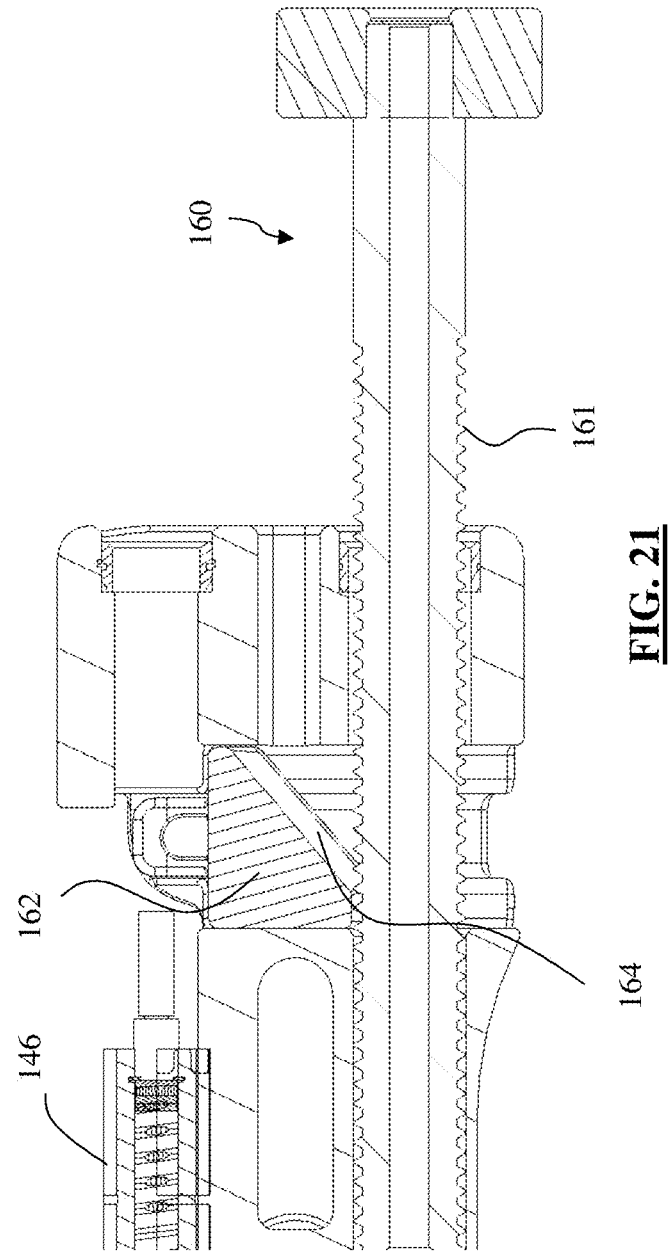
Figure 24:
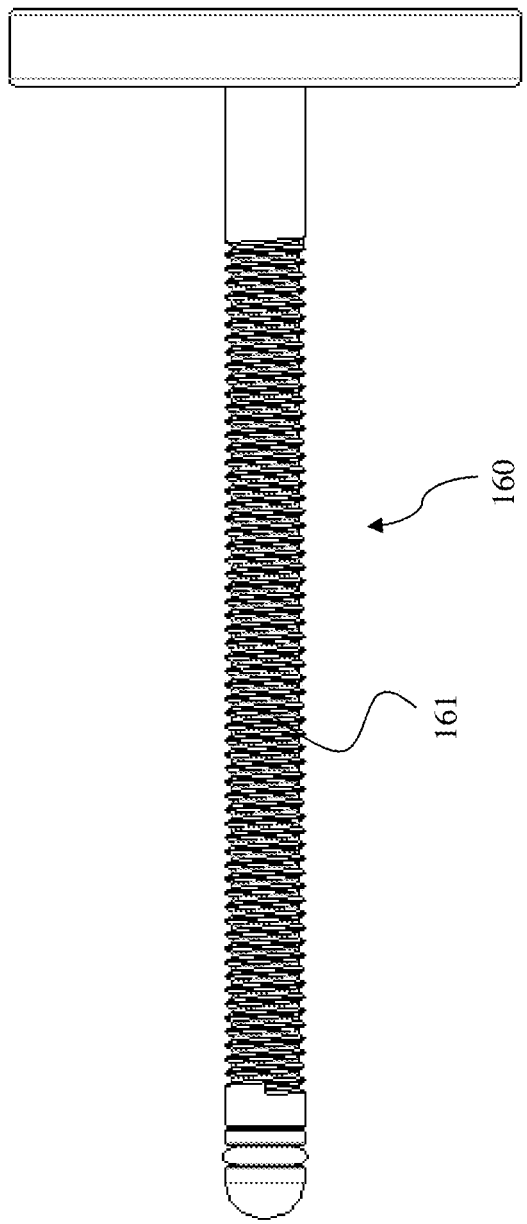
FIGS. 24 and 25 are side elevational and top sectional views, respectively, of the plunger shown in FIG. 23.
Figure 25:
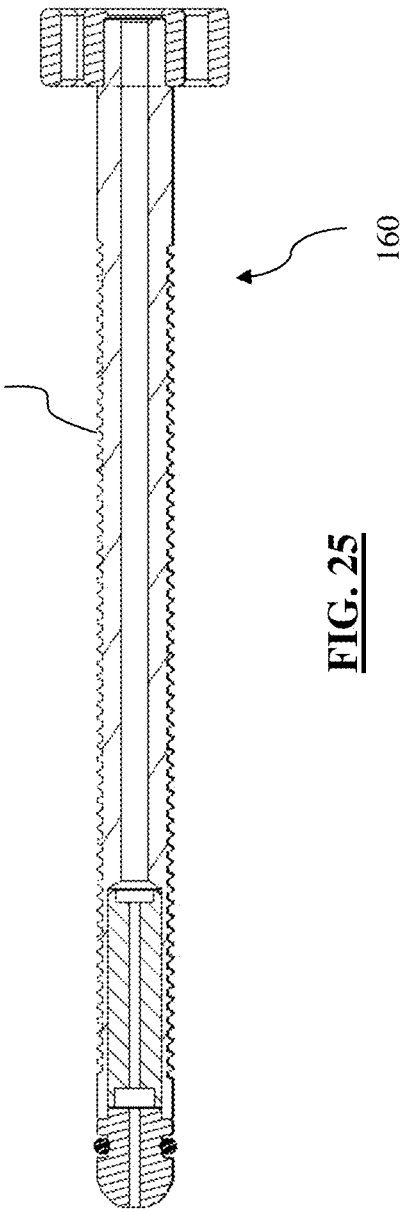
Figure 33:
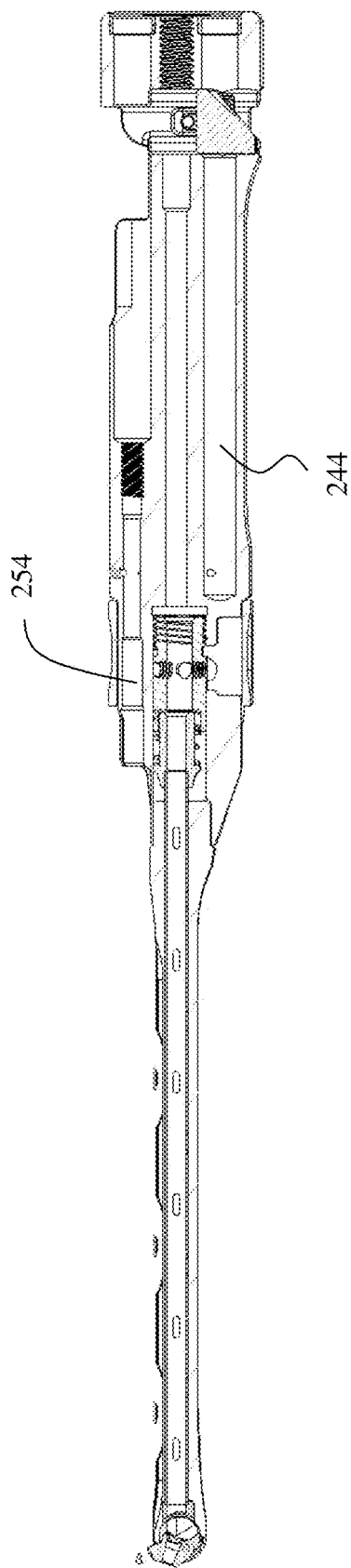
FIG. 33 is a side sectional view of the instrument shown in FIG. 28 taken along the line 33-33 of FIG. 30.
Figure 34:
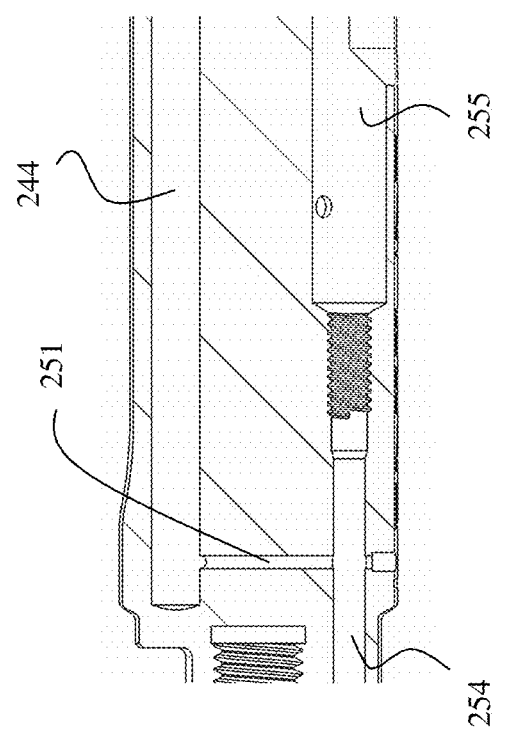
FIG. 34 is a portion of a side sectional view of the instrument shown in FIG. 28 taken along the line 34-34 of FIG. 31.

A valve 162 is positioned in handle to seal an aperture 163 of cavity 144. Valve 162 is movable between a lowered position, as shown in FIG. 20, in which cavity 144 is sealed, and a raised position, as shown in FIG. 21, in which access to cavity 144 is permitted. A tapered edge 164 of valve 162 allows plunger 160 to encounter valve 162 and move it from its lowered position to its raised position as plunger 160 is advanced into cavity 144, which occurs via a cavity extension 165. This configuration allows for valve 162 to uncover aperture 163 only when plunger 160 is present, which substantially prevents any leakage of fluid from cavity 144 during the introduction and use of plunger 160. Valve 162 is biased to its lowered position through a spring (not shown).

Figure 13:
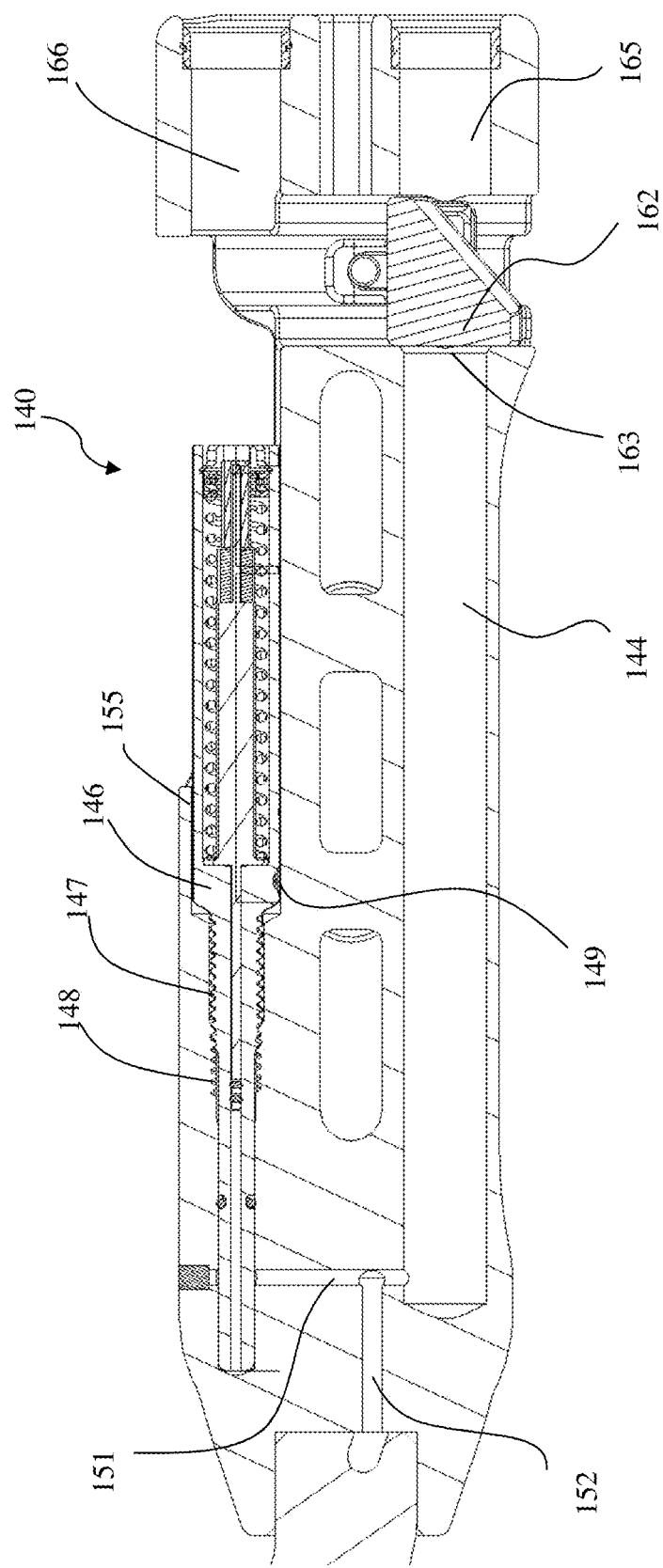
FIG. 13 is a side sectional view of a handle of the instrument shown in FIG. 1.
Figure 14:
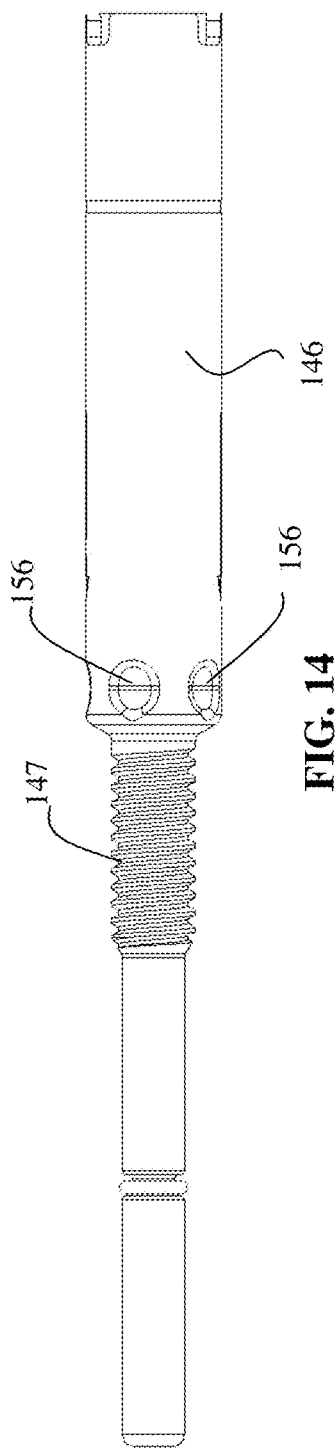
FIG. 14 is a side elevational view of a gauge of the instrument shown in FIG. 1.
Figure 15:
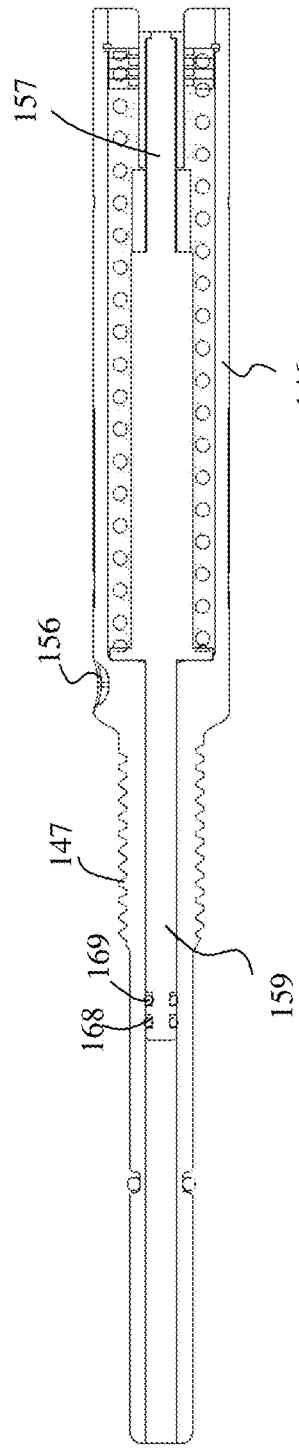
FIGS. 15 and 16 are side sectional views of the gauge shown in FIG. 14.
Figure 16:
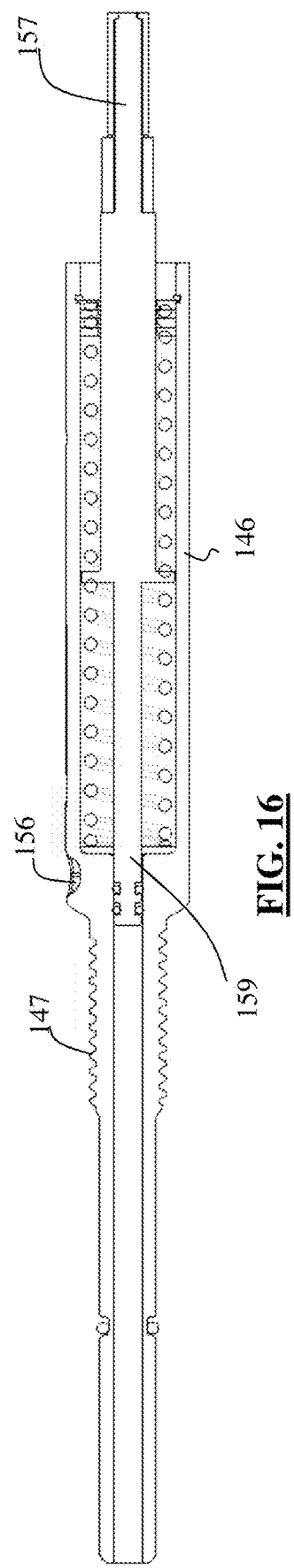

Instrument 100 includes a network of passages through which saline can travel toward tube set 182, and then through tube set 182 toward a connected surgical implant at a distal end of distal portion 111 of shaft 110. As shown in FIGS. 10 and 13, passages 151, 152, 153, and 154 connect cylindrical cavity 144 with tube set 182 within which unlock wire 188 resides. The dimensions of unlock wire 188 and tube set 182 are such that saline can flow around and past unlock wire 188 to ultimately flow out of distal exit port 184 and into a connected implant. While passage 151 is shown to be open at an external area of instrument 100, this allows for ease of manufacturing. That area can be plugged (as shown) or otherwise closed off to essentially close the passage so that only desired inlet and outlet portals exist within instrument 100.

As shown in FIGS. 13-16, a gauge 146 is integrated into the saline passageway to allow for determining its internal pressure. Gauge 146 is removable and is disposed within a channel 155 of handle 140 via a channel extension 166. External threads 147 on gauge 146 mate with internal threads 148 of channel 155 to secure gauge 146 to handle 140. A ball 149 disposed within channel 155 mates with one of several detents 156 of gauge 146 to provide tactile feedback that gauge 146 is seated to the proper extent when it is inserted into channel 155. A distal end of gauge 146 is open to allow saline to travel into gauge 146 via channels 151 and 155. In other embodiments, gauge 146 can be a permanent part of instrument 100.

Gauge 146 has a color-coded end 157 that can protrude outwardly depending on the magnitude of pressure within the passage system of instrument 100. Saline can enter gauge 146 through a lumen 158 at its distal end and then can communicate with a piston 159 that is connected with color-coded end 157. In this way, pressure in the internal fluid channels can manifest itself into movement of piston 159 to expose color-coded end 157 to an appropriate degree that identifies the amount of pressure within the internal fluid channels. When greater pressure exists, gauge 146 protrudes to a particular extent to reveal a color band through which the user can discern if a particular level of pressure has been reached in instrument 100. Piston 159 can have o-rings 168, 169 to prevent the fluid from moving past them within gauge 146.

The configuration of instrument 100 gives it an integrated design that streamlines the saline delivery as well as the pressure gauge into a single inserter/handle combination. One component that is disposable and replaceable is tube set 182. Plunger 160 and gauge 146 may also be disposable in different embodiments that are not shown. The elements of instrument 100, such as shaft 110, can be made of stainless steel or another biocompatible metal.

In use, instrument 100 facilitates insertion of an implant through an access instrument, such as a retractor or a tube used in MIS procedures. Instrument 100 is either assembled by the user or can come pre-assembled with shaft 110 secured to handle 140 and draw rod 119 loaded into shaft 110. Tube set 182 can also be preassembled or loaded by the user. Proximal attachable end 186 is loaded into a port in shaft 110, and distal exit port 184 is attached within recessed passage 116 of shaft 110 to expose distal exit port 184 at face 113. A flange 191 on a portion of proximal attachable end 186 fits into a slot within instrument 100 during insertion into the port in shaft 110. The slot can be linear to prevent rotation of proximal attachable end 186 within the port while still allowing for translation of proximal attachable end 186 along its axis within the port for insertion and removal. In other embodiments, the slot can be at least partially helical or circumferential to temporarily locked proximal attachable end in place. Implant collapse shaft 122 is threaded into aperture 120 so that together, tube set 184 and implant collapse shaft 122 seal off the internal passageway within shaft 110. This allows fluid from cavity 144 to be passed entirely through tube set 184. When implant collapse shaft 122 is first inserted, its marking is preferably aligned with the proximal mark of window 125 denoted with an "X" so that instrument 100 is in a configuration to expand the implant.

Gauge 146 is connected to handle 140 by passing it through channel extension 166 and into channel 155. Gauge 146 is rotated to engage external threads 147 with internal threads 148 of channel 155, and is advanced until ball 149 seats properly within one of detents 156.

A fluid, such as saline, is loaded into cylindrical cavity 144 of handle 140. This is done by using a syringe filled with saline in conjunction with a syringe extension 167, as shown in FIGS. 17-19. Syringe extension 167 includes an internal passage 170 and a mouth 171 to which the syringe is connected. Syringe extension 167 is passed through cavity extension 165 to encounter and move valve 162 to its raised position, as described above in connection with plunger 160. With internal passage 170 in communication with cavity 144, the syringe is emptied to load the saline into cavity 144. Additional saline can be provided and injected with the syringe until saline is produced at distal exit port 184 to ensure that no air is present in the instrument's internal passage or tube set 182. Syringe extension 167 is then removed, allowing valve 162 to move back to its lowered position to seal aperture 163 of cavity 144. Plunger 160 can then be introduced into cavity 144 the same way with toggle 142 engaged.

An implant is secured to face 113 of shaft 110. This includes aligning anti-rotation feature 115 with a corresponding cavity in the implant, and threading threaded rod 114 into a threaded hole of a surgical implant by rotating draw rod 119 from its proximal end to draw the implant flush against face 113. This positioning allows distal exit port 184 to communicate with a port on implant so that saline can be introduced into implant to facilitate expansion.

With the implant secured to instrument 100, the user can manipulate handle 140 to position the implant into the desired location of the disc space. This can occur through an access instrument, such as one of 18 mm diameter. During positioning, the user can impact surface 117 on the proximal end of proximal portion 112 of shaft 110.

Once in the desired position, the size of implant can be expanded through use of instrument 100. The user can locate toggle 142 in its disengaged position, if necessary, to more rapidly locate the plunger 160 in its most efficient position. Alternatively, this could be done when the instrument is assembled or prepared so that plunger 160 will be in its starting position at this point when it is first needed. Toggle 142 can then be moved to the engaged position so that plunger 160 can be rotated to advance it within cylindrical cavity 144, which forces saline to travel through the passage system, including passages 151-154, and tube set 182, and into a cavity within the surgical implant. The bayoneted shaft 110 improves visualization through the access instrument. Handle 140 is located away from the axis of the access instrument through which the procedure is performed, allowing greater visualization along that axis.

During this procedure, saline travels toward the implant and also into channel 155 to interact with gauge 146. Saline can enter lumen 158 by passing around the distal end of gauge 146 in channel 155. The pressure exerted on piston 159 by the saline can cause color-coded end 157 to protrude outward to indicate to the user via exposure of a color band as to the level of pressure that gauge 146 is reading. This allows the user to know if saline is being applied too rapidly or if the procedure is complete and the cavity in the implant is full. The main purpose of pressure gauge 146 is to monitor safety and not exceed pressure to the native tissue. When enough saline is passed, the user can move toggle 142 to its disengaged position, and more rapidly remove plunger 160.

In a separate embodiment, the pressure gauge housing can be a clear rigid plastic with marking indicating the fluid volume for assessing the relative displacement of fluid via action of the plunger into the implant, which could indicate incremental expansion of the implant.

If the surgeon wishes to collapse the implant during the procedure, implant collapse shaft 122 is threaded distally until the distal mark of window 125 denoted with a "C" is aligned with the marking on implant collapse shaft 122. This position may also coincide with implant collapse shaft 122 abutting an internal surface of shaft 110 to prevent further distal movement of unlock wire 188. In this configuration, the implant can be collapsed from its expanded position. This is facilitated by the distal end of unlock wire 188 engaging a mechanism of the implant that releases a structure that otherwise maintains its expanded configuration. Collapsing or reducing the size of the implant typically includes the saline disposed within the implant being passed back into instrument 100. Plunger 160 can be rotated proximally to allow the saline back into instrument 100.

With the implant in its finally implanted (and preferably expanded) position, the implant can be disengaged from instrument 100. This includes rotating draw rod 119 so that threaded rod 114 is drawn out of the threaded hole of the implant. Once disengaged from the implant, unlock wire 188 can be translated distally by unthreading implant collapse shaft 122 to a location in which the distal end of unlock wire 188 plugs distal exit port 184 to prevent leakage of any remaining saline in the system. Instrument 100 can then simply be removed from the surgical site. Plunger 160 can then be quickly removed from instrument 100 by moving toggle 142 to its disengaged position. Tube set 184 can then be removed and discarded so that the remaining components of instrument 100 can be sterilized for reuse.

A second embodiment of a surgical instrument 200 is depicted in FIGS. 28-46. Instrument 200 is similar in its functionality with respect to a surgical implant, but it allows for different angles to be created between the axis of instrument 200 and the axis of the surgical implant. Certain of the features of instrument 200 are similar to those of instrument 100, and accordingly, are like numbered.

Instrument 200 includes a shaft 210 and a handle 240 that together extend generally along a single axis. In other embodiments, instrument 200 may be bayoneted. A distal portion 211 of shaft 210 has an integrated junction block 270 that is pivotally connected with shaft 210. A distal end of junction block 270 includes a face 213 from which a threaded rod 214 of a draw rod 219 protrudes through an aperture 278, as shown in FIGS. 37-40. Face 213 is configured to substantially match a curve of the corresponding implant to make the connection flush. Rod 214 can be engaged with a threaded hole of a surgical implant. An anti-rotation feature 215 is also disposed on face 213. A portal 271 is provided through which a tube set can be connected, as discussed below.

Figure 35:
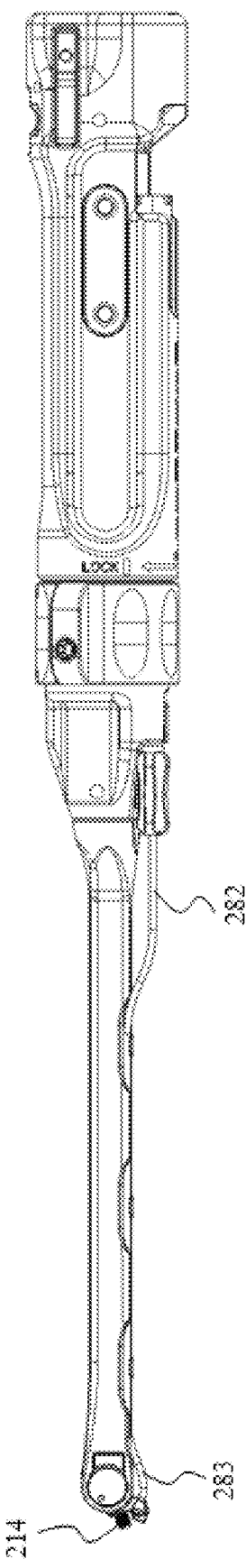
FIGS. 35 and 36 are top plan views of the instrument shown in FIG. 28.
Figure 36:
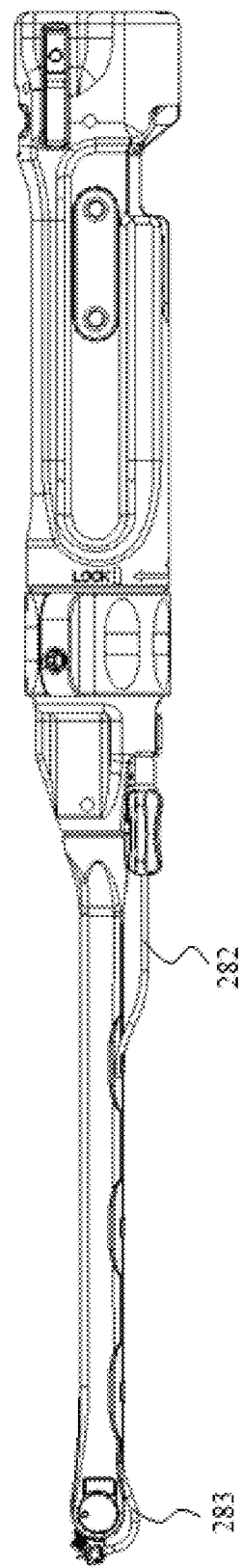
Figure 46:
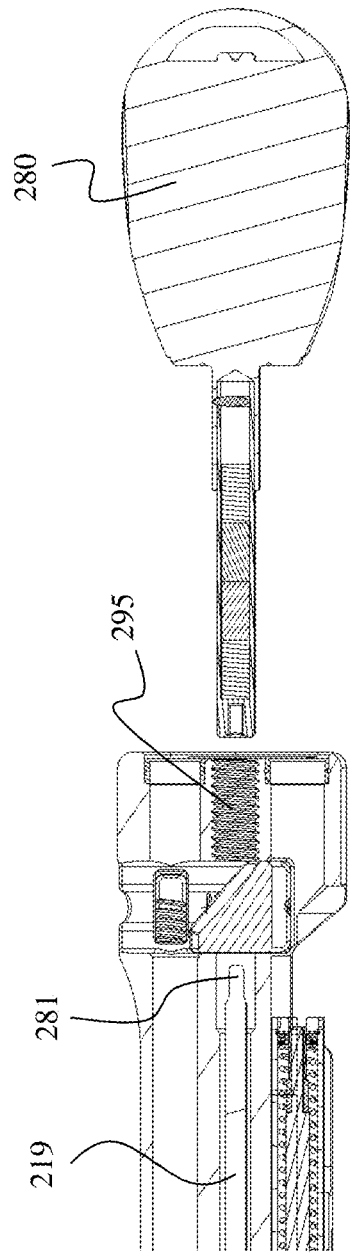
FIG. 46 is a side sectional view of a proximal portion of the handle of the instrument shown in FIG. 28 used with a tool.

Junction block 270 is connected with a rotatable housing 272 that is disposed within a cylindrical cavity of distal portion 211 of shaft 210. This allows junction block 270 to rotate about the end of shaft 210 within a slot 273 to different orientations with respect to the axis of shaft 210, as shown in FIGS. 35 and 36. Draw rod 219 extends through shaft 210 and rotatable housing 272. It can accommodate the different angled positions of junction block 270 due to a U-joint 274 that allows for angles between threaded rod 214 and a proximal portion of draw rod 219. Draw rod 219 is rotated via a tool 280, as shown in FIG. 46. A proximal end of draw rod 219 can have a hex-head 281 or other geometric configuration that mates with tool 280. Tool 280 can be inserted through a threaded hole 295 at a proximal end of handle 240 to engage hex-head 281, as shown in FIG. 46. Because tool 280 is not used simultaneously with plunger 260, valve 262 will be in its lowered position when tool 280 is used so that valve 262 does not impede the use of tool 280. Threaded hole 295 can also be connected with a slap hammer or strike plate to assist with inserting or removing an attached implant with respect to the intervertebral space.

Figure 38:
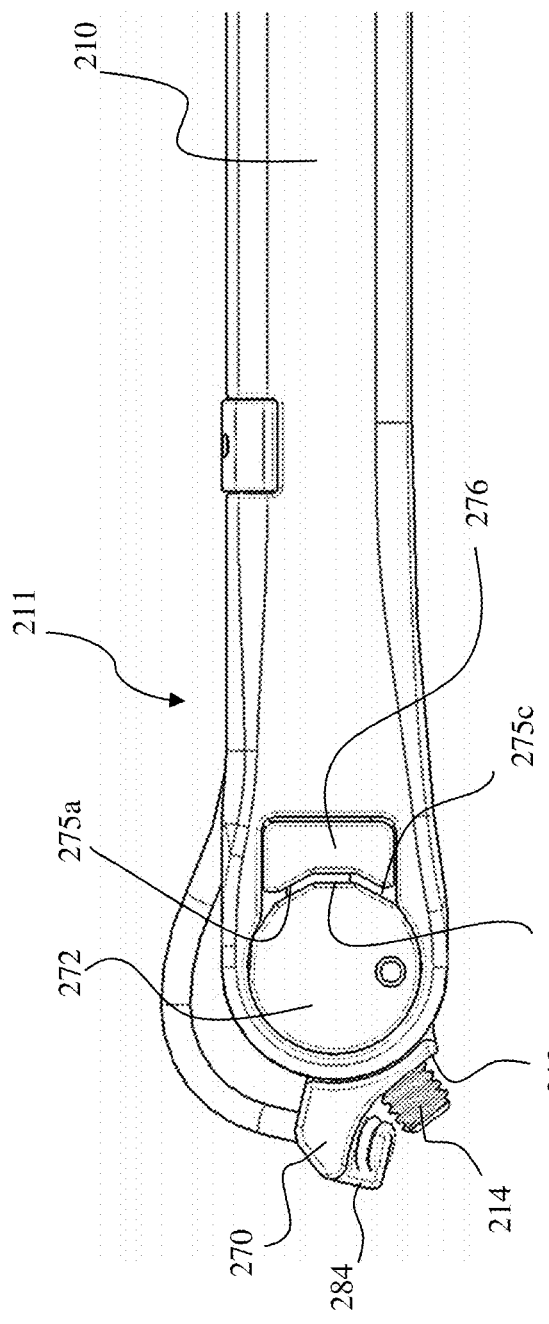
FIGS. 38 and 39 are top plan views of a distal portion of the instrument shown in FIG. 28.
Figure 39:
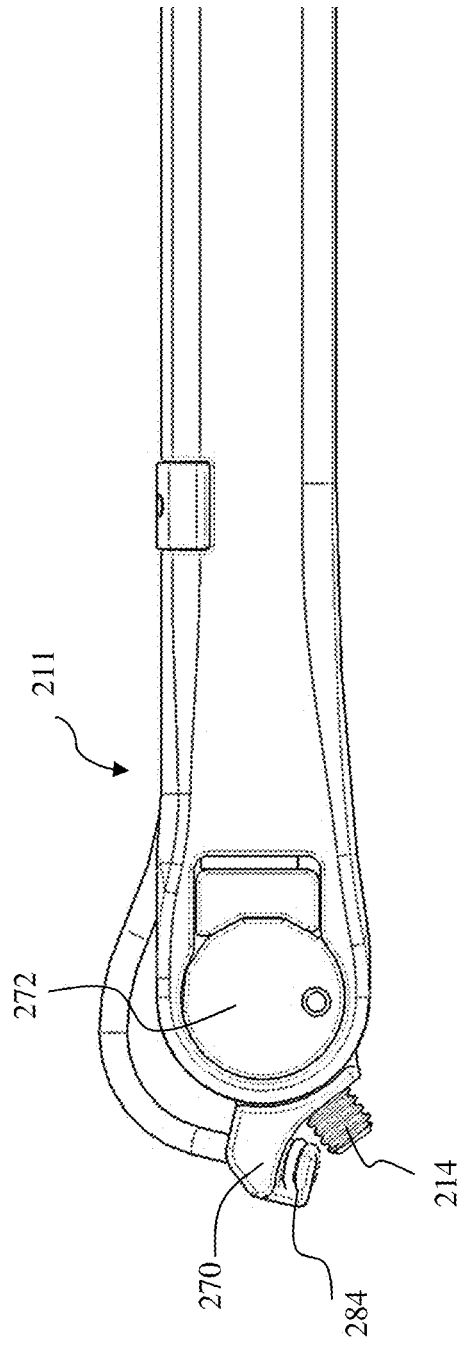
Figure 40:
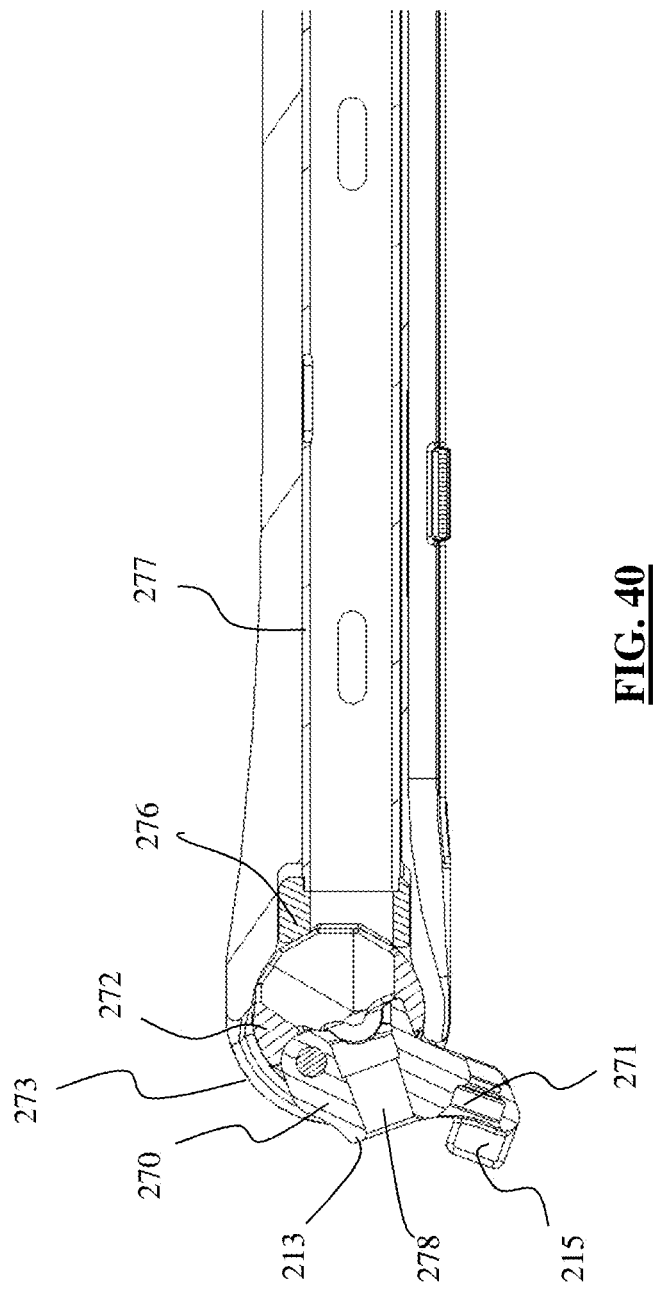
FIG. 40 is a top sectional view of a distal portion of the instrument shown in FIG. 28.
Figure 41:
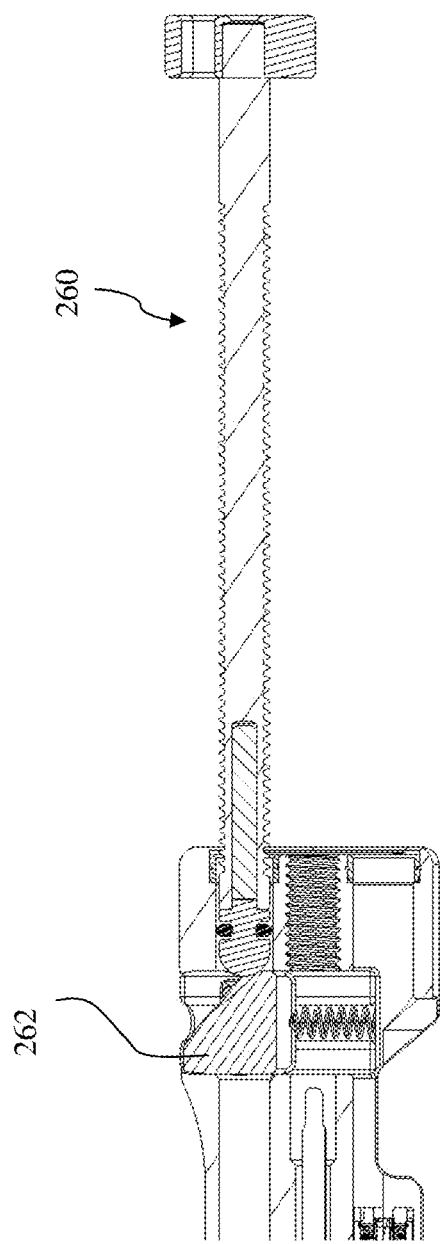
FIGS. 41 and 42 are side sectional views of a proximal portion of the handle of the instrument shown in FIG. 28 used with a plunger.
Figure 42:
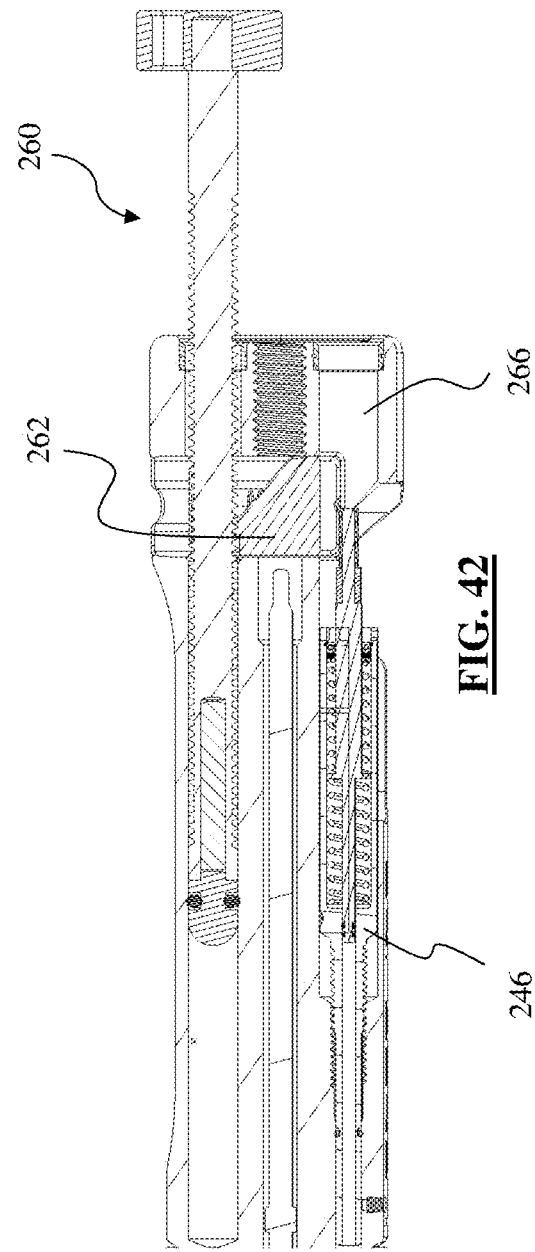

A proximal aspect of rotatable housing 272 has three facets 275a-c that can mate with corresponding facets of a block 276 of shaft 210. The facets can be more or fewer in number, and can also be non-planar. Block 276 is advanced along the axis of shaft 210 via its connection with a hollow cylinder 277 that is disposed in shaft 210 and within which draw rod 219 is disposed. A collar 279 of instrument 200 is disposed between shaft 210 and handle 240. Rotation of collar 279 translates hollow cylinder 277, thus moving block 276 to lock the tip angle. When block 276 is moved proximally, a gap exists between block 276 and rotatable housing 272, as shown in FIG. 38, allowing rotation of rotatable housing 272 within shaft 210. When block 276 is moved distally as shown in FIG. 39, the gap is closed and the facets are preferably engaged to temporarily secure the position of rotatable housing 272 within shaft 210 and to prevent it from rotating. Threaded rod 214 can pivot from a starting angle (for example, an angle of about 20 degrees on one side of the axis of draw rod 219) through a final angle (for example, and angle of about 77 degrees on the other side of the axis of draw rod 219, i.e. through a total angular range of about 97 degrees). A laser mark and/or ridge on collar 279 can align with a feature or mark on instrument 200 to indicate when rotatable housing 272 is locked and/or unlocked. In other embodiments, there are no mating facets between rotatable housing 272 and block 276, and rotatable housing 272 and block 276 each have round or curved surfaces that can mate and be locked by friction.

Cylindrical cavity 244 of handle 240 is configured to hold saline, as discussed above in connection with instrument 100. Saline is forced through cylindrical cavity 244 by plunger 260, and then out through passages 251 and 254 that connect cavity 244 with a tube set 282. Plunger 260 can be the same plunger 160 configured to work with both instruments 100 and 200.

Figure 37:
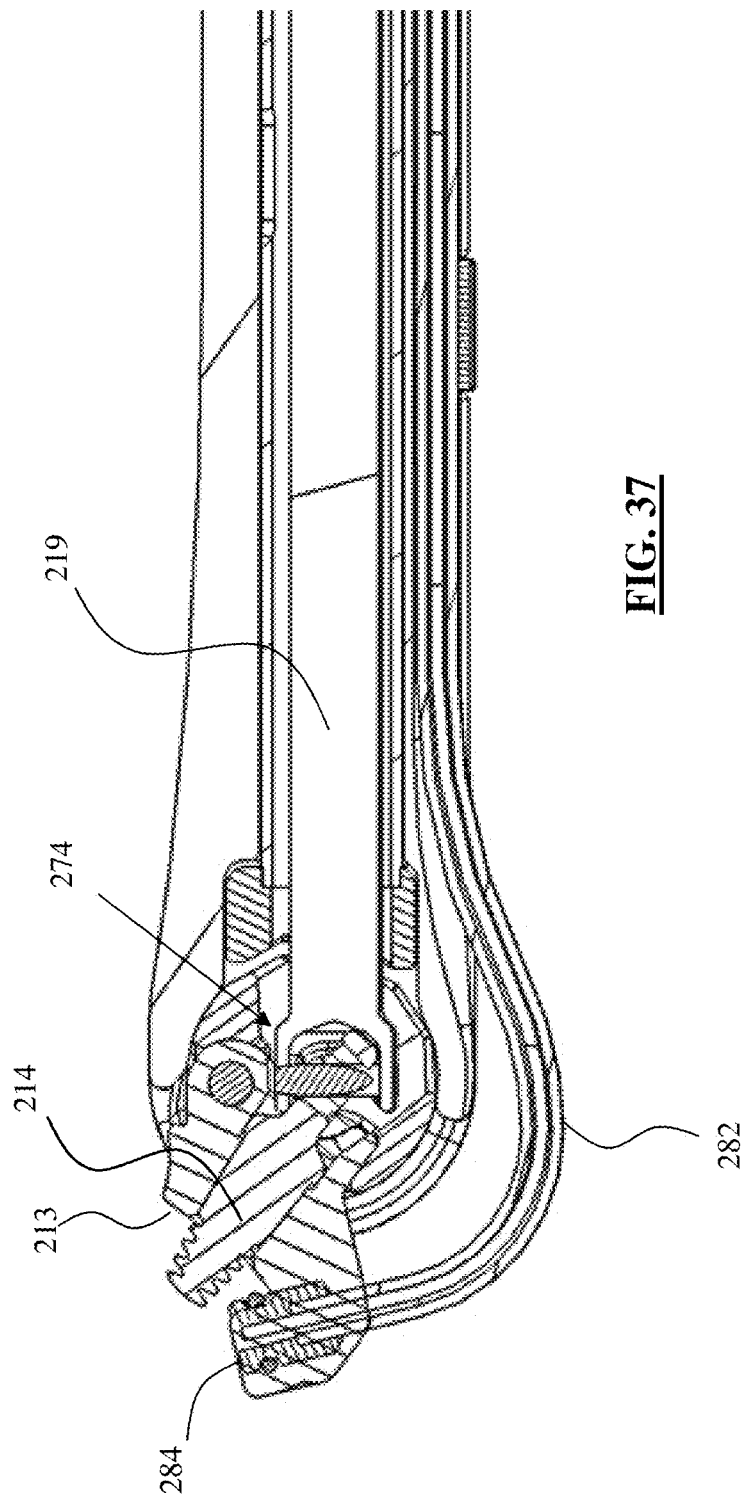
FIG. 37 is a top sectional view of a distal portion of the instrument shown in FIG. 28.

Tube set 282 can be identical to tube set 182 described above so that it can be used with either of instruments 100 or 200. Proximal attachable end 286 can be loaded into a port, such as passage 254, in handle 240 such that the aspects of tube set 282 located proximally of o-ring 287 are in communication with the saline delivery system within handle 240. As shown in FIGS. 37-39, distal exit port 284 is configured to be attached within portal 271 of junction block 270. Thus, as junction block 270 rotates, distal exit port 284 rotates with it. Flexible tube 283 of tube set 282 may have some slack to account for this rotation, and may also slide or otherwise move within recessed passage 216 along shaft 210 to accommodate such movement of distal exit port 284. Passage 216 has a groove and hook configuration to secure flexible tube 283 while allowing movement of same therein. Proximal attachable end 286 can also move within passage 254 during such movement, as shown in FIGS. 35 and 36, while maintaining a seal with passage 254 due to o-ring 287. A flange, similar to flange 191 discussed above, on a portion of proximal attachable end 286 fits into a slot within instrument 200 during insertion into the port in shaft 210. The slot can be linear to prevent rotation of proximal attachable end 286 within the port and to facilitate translation of proximal attachable end 186 along its axis within the port for insertion and removal and during operation of instrument 200, as described below.

Figure 45:
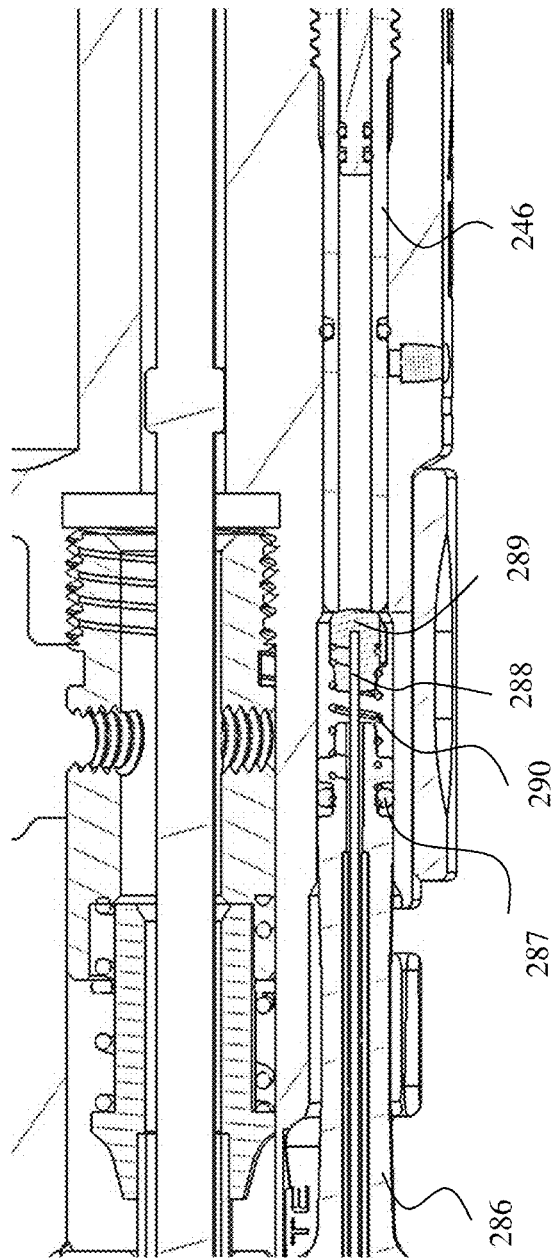
FIG. 45 is a side sectional view of a portion of the handle of the instrument and a tube set shown in FIG. 28.

As shown in FIGS. 43-45, a gauge 246 is integrated into the saline passageway and is similar to that described above in connection with instrument 100. Gauge 246 is removably disposed within a channel 255 of handle 240 via a channel extension 266 and threaded into place as described above. In instrument 200, gauge 246 is in line with tube set 282 such that a distal end of gauge 246 is in communication with proximal knob 289 of tube set 282, which is in turn connected with an unlock wire 288 and is separated from a proximal end of proximal attachable end 286 via a spring 290, as shown in FIG. 45. Gauge 246 can be advanced distally within channel 255 via engagement by a driver 223, shown in FIG. 44. When advanced, a distal end of gauge 246 engages knob 289 of tube set 282 to advance unlock wire 288 distally. Markings on an outer portion of handle 210, as shown in FIG. 28, can align with a portion or marking on gauge 246 when unlock wire 288 is in position to collapse the surgical implant and when unlock wire 188 is in position to allow expansion of the surgical implant.

Handle 240 includes a toggle 242 and a valve 262 that are configured similarly and operate similarly with their counterparts in instrument 100 to interact with plunger 260.

In use, instrument 200 functions in a generally similar manner to instrument 100. Instrument 200 can be provided pre-assembled or can be assembled by the user. This includes securing shaft 210 to handle 240 and loading tube set 282 into handle 240 and junction block 270. Draw rod 219 can also be loaded into its respective channel. Gauge 246 is connected to handle 240 in its working position. Cylindrical cavity 244 of handle 240 can either be pre-loaded with saline, or cylindrical cavity 244 can be loaded with saline by the user in the same manner as described above with respect to syringe extension 167.

Next, an implant is secured to face 213. This includes aligning anti-rotation feature 215 with a corresponding cavity in implant, and threading threaded rod 214 into a threaded hole of the implant by rotating draw rod 219 from its proximal end to draw the implant flush against face 213. This positioning allows distal exit port 284, including o-ring 285, to communicate with a port on the implant so that saline can be introduced into implant to facilitate expansion.

With the implant secured to instrument 200, the user can manipulate handle 240 through an access instrument, such as a retractor or a tube, to position the implant into the desired location of the disc space. During positioning, the user can impact the surface on the proximal end of handle 240. The implant and junction block 270 can be repositioned at the end of shaft 210 to allow a user to more accurately access the disc space and position the implant in the proper and intended location in the disc space. This may involve locking and unlocking the connection between rotatable housing 272 (to which the implant is coupled) and block 276 via rotation of collar 279. When locked, the facets of rotatable housing 272 and block 276 may be aligned to prevent rotation of rotatable housing 272. When unlocked, rotation of the implant about the distal portion of shaft 210 is allowed. The surgeon, at his or her discretion, can use this locking and unlocking feature to aid in achieving the desired final location of the implant.

Once in the desired position, the implant can be expanded through use of instrument 200. Toggle 242 can be moved to its engaged position with respect to plunger 260. Plunger 260 can then be rotated to advance it within cylindrical cavity 244, which forces saline to travel out of cylindrical cavity 244, through tube set 282, and into a cavity within the surgical implant. During this procedure, saline also travels through channel 255 and into communication with gauge 246 to advise or alert the user via exposure of a color band, markings, or features as to the level of pressure.

If the surgeon wishes to collapse the implant during the procedure, gauge 246 is threaded distally, which can be guided by aligning a marking or feature of gauge 246 with a mark on handle 240. This forces knob 289 and thus nitinol wire 288 distally. In this configuration, instrument 200 is in a configuration in which the implant can be collapsed from its expanded position. This is facilitated by the distal end of nitinol wire 288 engaging a mechanism of the implant that releases a structure that otherwise maintains its expanded configuration. Plunger 260 can be rotated proximally to aid in drawing the saline back into instrument 200. As gauge 246 is threaded proximally, spring 290 moves nitinol wire 288 back into its resting state. The force exerted on knob 289 by gauge 246 is less than the force of o-ring 287 within channel 255, so that movement of gauge 289 does not correspond with movement of proximal attachable end 286 within channel 255.

With the implant in its final position, the implant can be disengaged from instrument 200. This includes rotating draw rod 219 so that threaded rod 214 is drawn out of the threaded hole of the implant. Instrument 200 can then simply be removed from the surgical site.

Figure 47:
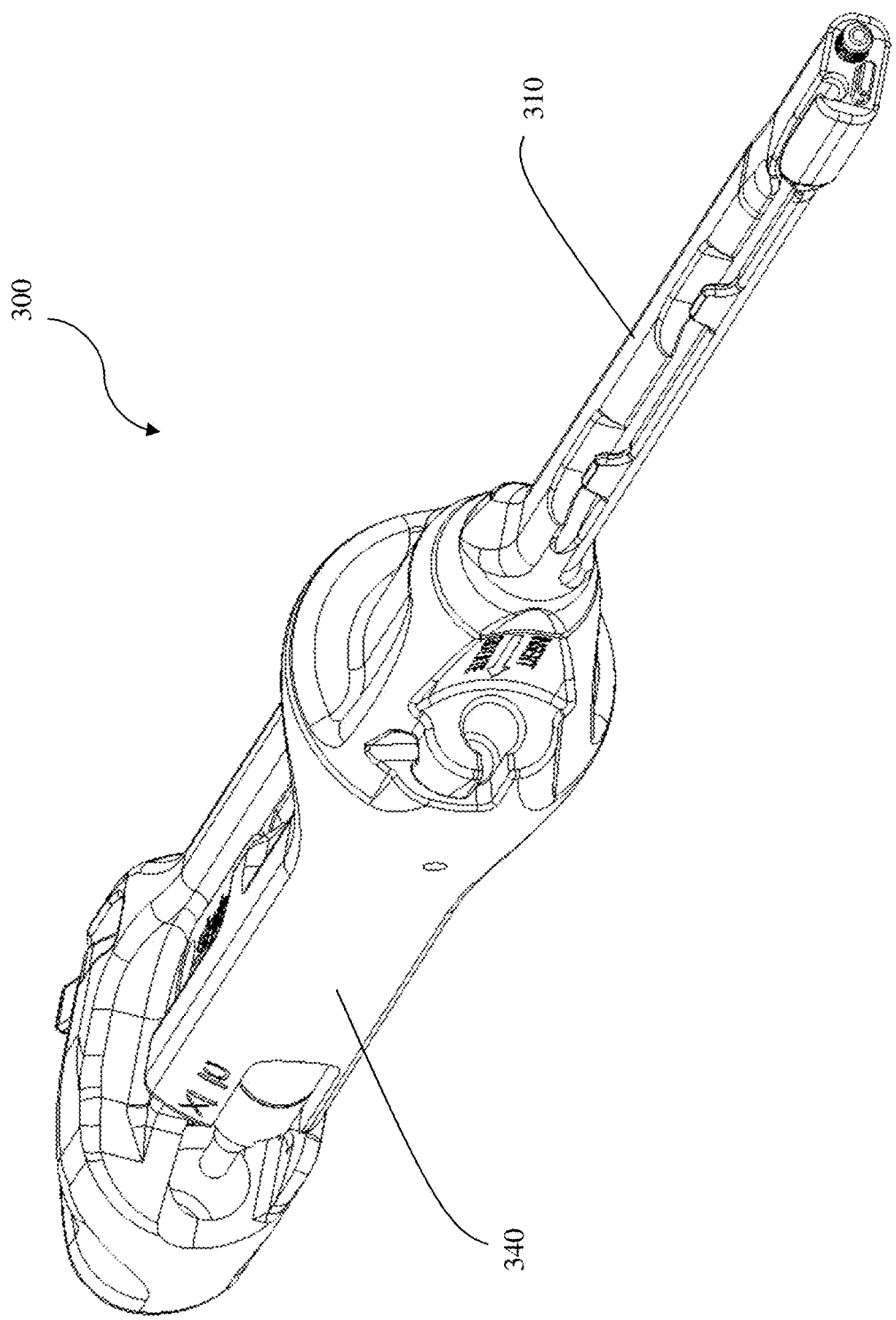
FIGS. 47-49 are front, rear, and side perspective views, respectively, of a surgical instrument in accordance with another embodiment of the present invention.
Figure 48:
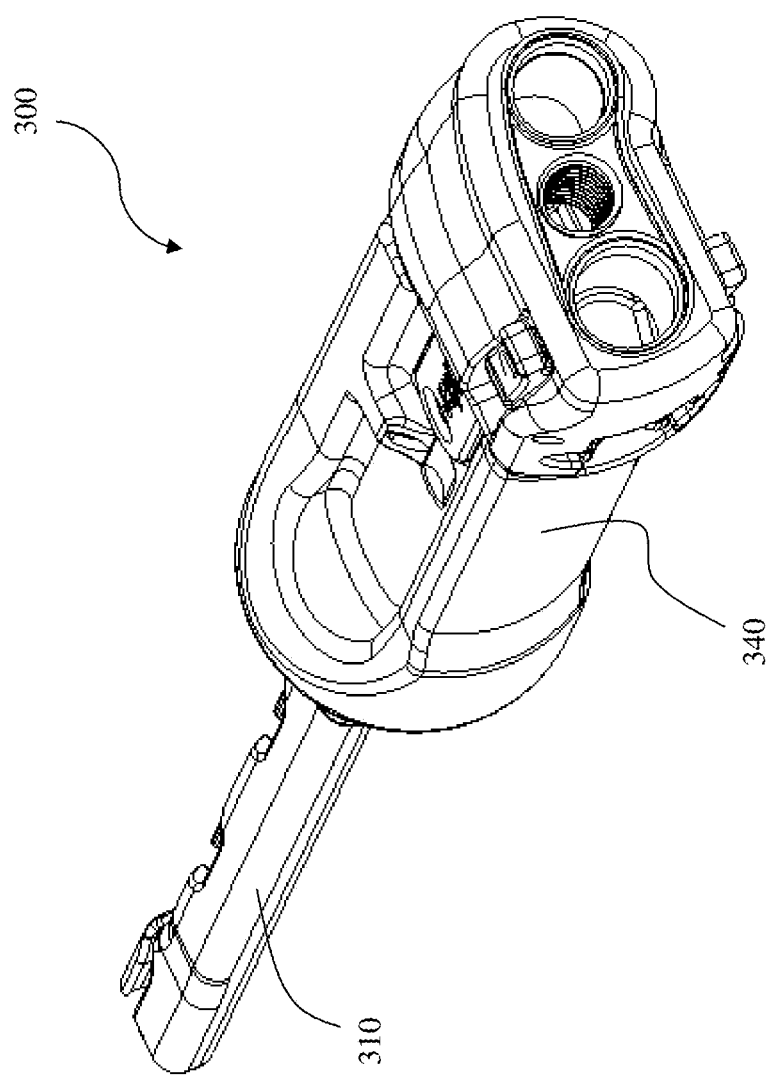
Figure 49:
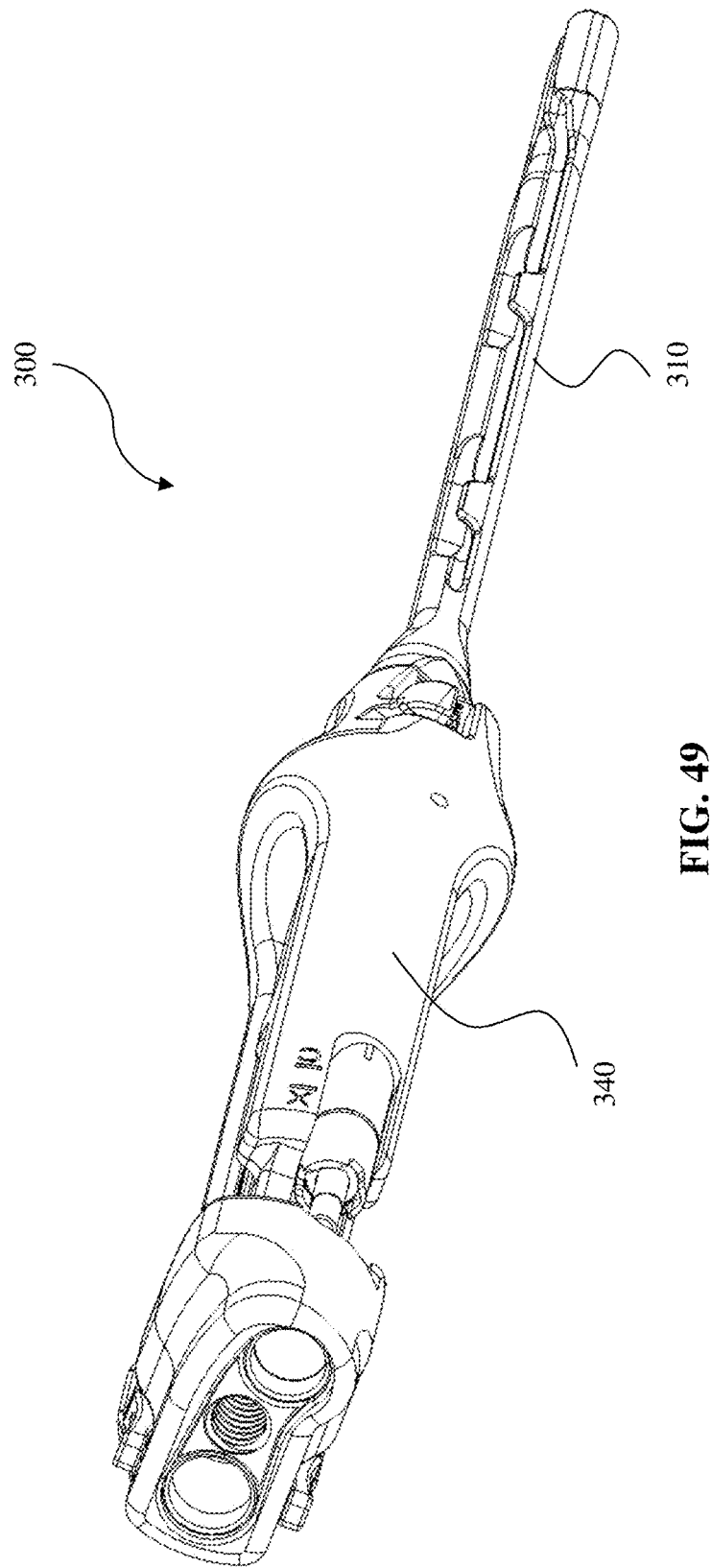

A third embodiment of a surgical instrument 300 is depicted in FIGS. 47-49. Instrument 300 includes a handle 340 that is very similar in configuration and operation to handle 240 of instrument 200. Instrument also includes a shaft 310 that is very similar in configuration and operation to shaft 110 of instrument 100. Instrument 300 does not have a rotatable component at its distal end and is not bayonetted. Otherwise, the features and functions of instrument 300 are as described above in connection with instruments 100 and 200.

Any of the present instruments 100, 200, and/or 300 can be provided in a kit with a corresponding spinal implant, which is expandable through the introduction of the fluid therein.

The instruments and the components thereof disclosed herein can be made of any rigid biocompatible materials or combinations thereof, such as a plastic, PEEK, Radel, Silastic and any various grades of stainless steel for medical application. The seals (o-rings or custom seals) can be made of any biocompatible medical grade elastomeric materials with elastic properties. For example, the gauge housing may be made of a transparent plastic. The syringe body may be made of a transparent plastic insert held within the cavity of the handle with a side window for viewing fluid displacement.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical instrument comprising:
a shaft having a distal end connectable with an implant; and
a handle rigidly connected to a proximal end of the shaft, wherein the instrument defines an internal fluid channel through which a fluid can be passed,
a tubular duct having a proximal end configured to connect to the instrument to communicate with the internal fluid channel and a distal end configured to connect to the distal end of the shaft and to engage the implant to allow passage of a fluid from the internal fluid channel to the implant,
wherein the shaft includes a recessed passage in its outer surface in which a portion of the tubular duct can be disposed.

2. The surgical instrument of claim 1, wherein the internal fluid channel includes a cavity in the handle, and the handle includes an aperture in a proximal portion of the handle that is in communication with the cavity.

3. The surgical instrument of claim 2, wherein the handle includes a movable valve configured to seal the cavity at the aperture.

4. The surgical instrument of claim 2, further comprising a plunger movable within the cavity to force fluid from the aperture to a distal portion of the cavity.

5. The surgical instrument of claim 4, wherein the handle includes a toggle having an internally threaded section configured to selectively engage an externally threaded section of the plunger.

6. The surgical instrument of claim 5, wherein when the toggle is in an engaged position, the plunger can only move within the cavity by rotating the plunger to engage the externally threaded section of the plunger with the internally threaded section of the toggle, and when the toggle is in a disengaged position, the plunger can move freely within the cavity.

7. The surgical instrument of claim 5, wherein the toggle includes opposing first and second toggle clips.

8. The surgical instrument of claim 1, wherein the proximal end of the tubular duct is at least partially disposed within a passage of the handle.

9. The surgical instrument of claim 1, wherein the tubular duct is configured to move along the shaft within the recessed passage.

10. The surgical instrument of claim 1, wherein the tubular duct includes a wire disposed within a tube, wherein the wire is movable between a proximal position and a distal position, the wire being configured to cooperate with a mechanism of the implant when in the distal position.

11. The surgical instrument of claim 10, wherein the wire is spring biased to the proximal position.

12. The surgical instrument of claim 10, further comprising a gauge in communication with the fluid channel and configured to indicate pressure within the fluid channel, wherein the gauge is movable within a gauge cavity in the handle and can be advanced to move the wire from the proximal position to the distal position.

13. The surgical instrument of claim 10, further comprising a collapse shaft movable within a cavity in the handle, wherein the collapse shaft can be advanced to move the wire from the proximal position to the distal position.

14. The surgical instrument of claim 1, further comprising a gauge in communication with the fluid channel and configured to indicate pressure within the fluid channel.

15. The surgical instrument of claim 1, wherein the handle extends along an axis that is angled with respect to an axis along which the shaft extends.

16. A kit comprising:
the surgical instrument of claim 1; and
a spinal implant that is expandable through the introduction of the fluid therein.

17. The surgical instrument of claim 1, wherein at least a portion of the tubular duct between its proximal and distal ends extends along and outside the shaft.

18. The surgical instrument of claim 1, wherein the surgical instrument further comprises a rod disposed within at least a portion of the shaft and having a threaded distal end for attaching to the implant.

19. A surgical instrument comprising:
a shaft having a distal end connectable with an implant; and
a handle rigidly connected to a proximal end of the shaft, wherein the instrument defines an internal fluid channel through which a fluid can be passed,
a tubular duct having a proximal end configured to connect to the instrument to communicate with the internal fluid channel and a distal end configured to connect to the distal end of the shaft and to engage the implant to allow passage of a fluid from the internal fluid channel to the implant,
wherein the proximal end of the tubular duct is at least partially disposed within a passage of the shaft.

20. A surgical instrument comprising:
a shaft having a distal end connectable with an implant;
a handle rigidly connected to a proximal end of the shaft; and
a plunger,
wherein the instrument defines an internal fluid channel through which a fluid can be passed,
wherein the internal fluid channel includes a cavity in the handle, and the handle includes an aperture in a proximal portion of the handle that is in communication with the cavity,
wherein the handle includes a movable valve configured to seal the cavity at the aperture,
wherein the plunger is movable within the cavity to force fluid from the aperture to a distal portion of the cavity, and
wherein the handle extends along an axis that is angled with respect to an axis along which the shaft extends.

* * * * *